(12) United States Patent
Wyatt

(10) Patent No.: US 7,841,718 B2
(45) Date of Patent: Nov. 30, 2010

(54) APPARATUS AND METHOD FOR ASSESSING RETINAL DAMAGE

(75) Inventor: Harry J. Wyatt, New York, NY (US)

(73) Assignee: The Research Foundation of State University of New York, Albany, NY (US)

(*) Notice: Subject to any disclaimer, the term of this patent is extended or adjusted under 35 U.S.C. 154(b) by 32 days.

(21) Appl. No.: 12/429,628

(22) Filed: Apr. 24, 2009

(65) Prior Publication Data

US 2009/0237614 A1 Sep. 24, 2009

Related U.S. Application Data

(62) Division of application No. 10/972,613, filed on Oct. 25, 2004, now Pat. No. 7,524,064.

(60) Provisional application No. 60/551,649, filed on Mar. 9, 2004.

(51) Int. Cl.
*A61B 3/10* (2006.01)
(52) U.S. Cl. .................. 351/211; 351/221; 351/204
(58) Field of Classification Search .............. 351/204, 351/211, 221, 216, 222
See application file for complete search history.

(56) References Cited

U.S. PATENT DOCUMENTS

| | | | |
|---|---|---|---|
| 4,861,154 A | 8/1989 | Sherwin et al. | |
| 5,065,767 A | 11/1991 | Maddess et al. | |
| 5,233,373 A | 8/1993 | Peters et al. | |
| 5,233,517 A | 8/1993 | Jindra | |
| 5,295,495 A | 3/1994 | Maddess et al. | |
| 5,422,352 A | 6/1995 | Astrup et al. | |
| 5,539,482 A | 7/1996 | James et al. | |
| 5,912,723 A | 6/1999 | Maddess et al. | |
| 5,963,300 A | 10/1999 | Horwitz | |
| 6,068,377 A | 5/2000 | McKinnon et al. | |
| 6,162,186 A | 12/2000 | Scinto et al. | |
| 6,227,668 B1 | 5/2001 | McKinnon et al. | |

(Continued)

OTHER PUBLICATIONS

Gilpin, L.B., et al., "Threshold variability using different Goldmann stimulus sizes," Acta. Opthamol. (Copenh.), pp. 674-676 (1990).

(Continued)

*Primary Examiner*—Ricky L Mack
*Assistant Examiner*—Brandi N Thomas
(74) *Attorney, Agent, or Firm*—Wilmer Cutler Pickering Hale & Dorr LLP.

(57) ABSTRACT

The invention administers an objective clinical test to an eye that measures the visual sensitivity of the superior retina and the inferior retina, by alternately presenting a stimulus pair comprising a shaped superior light stimulus and a shaped inferior light stimulus that are horizontal mirror images of one another and have shapes encompassing visual field defects. The shaped superior and inferior light stimuli stimulate pupillary responses whose amplitudes are measured. A cycle-averaged pupillary response balance and a luminance ratio are computed for each presentation of a stimulus pair. A stimulus pair response curve is computed by fitting cycle-averaged pupillary response balances to a sigmoid function of the luminance ratios. A balanced luminance ratio at which the cycle-averaged pupillary response balance is equal to about zero is computed from the sigmoid function. The balanced luminance ratio is indicative of the presence and location of retinal nerve damage.

17 Claims, 16 Drawing Sheets

U.S. PATENT DOCUMENTS

| | | | |
|---|---|---|---|
| 6,276,798 B1 | 8/2001 | Gil et al. |
| 6,315,414 B1 | 11/2001 | Maddess et al. |
| 6,356,036 B1 | 3/2002 | Zhou |
| 6,556,853 B1 | 4/2003 | Cabib et al. |
| 6,652,459 B2 | 11/2003 | Payne et al. |
| 6,709,109 B1 | 3/2004 | Richards et al. |
| 6,735,331 B1 | 5/2004 | Binnun et al. |
| 6,758,823 B2 | 7/2004 | Pasquale et al. |
| 7,006,863 B2 | 2/2006 | Maddess et al. |

OTHER PUBLICATIONS

Glovinsky, Y. et al., "Retinal ganglion cell loss is size dependent in experiment glaucoma," Invest. Opthalmol. Vis. Sci., pp. 484-491 (1991).

Glovinsky, Y. et al., "Foveal ganglion cell loss is size dependent in experimental glaucoma," Invest. Opthalmol. Vis. Sci., pp. 395-400 (1993).

Hart, W.M. et al., "The onset of evolution of glaucomatous visual field defects," Opthalmology, pp. 268-279 (1982).

Harwerth, R.S., et al., "Ganglion cell losses underlying visual field defects from experimental glaucoma," Invest. Opthalmol. Vis. Sci., pp. 2242-2250 (1999).

Heijl, A. et al., "Automatic perimetry (COMPETER), Ability to detect early glocomatous field defects," Arch. Opthalmol., pp. 1560-1563 (1980).

Heijl, A. et al., "Test-retest variability in glacomatous visual fields," Am. J. Opthalmol., pp. 130-135 (1989).

Heijl, A. et al., "Normal variability of static perimetric threshold values across the central visual field," Arch. Opthalmol., pp. 1544-1549 (1987).

Heijl, A. et al., "The frequency distribution of earliest glacomatous visual field defects documented by authomatic perimtry," Acta. Opthalmol. (Copenh.), pp. 658-664 (1984).

Hultborn, H. et al., "The neuronal pathway subserving the pupillary light reflex," Brain Res., pp. 255-267 (1978).

Johnson, C.A. et al., "Screening for glaucomatous visual field loss with frequency-doubling perimetry," Ophthalmology, pp. 413-425 (1997).

Johnson, L.N. et al., "Correlation of afferent pupillary defect with visual field loss on automated perimetry," Opthalmology, pp. 1649-1655 (1988).

Jonas, J.B. et al., "Count and density of human retinal photoreceptors," Graefes Arch. Clin. Exp. Opthalmol., pp. 505-510 (1992).

Junemann, A.G. et al., "Quantitative analysis of visual field and optic disk in glaucoma: retinal nerve fiber bundle-associated analysis," Graefes Arch. Clin. Exp. Opthamol., pp. 306-314 (2000).

Kardon, R. "Pupillary light reflex," Curr. Opin. Opthalmol., pp. 20-26 (1995).

Kardon, R. "Pupil perimetry," Curr. Opin. Opthalmol., pp. 565-570 (1992).

Kardon, R.H. et al, "Automated pupil perimetry. Pupil field mapping in patients in normal subjects," Opthalmology, pp. 485-495 (1991).

Kardon, R. et al., "Pupil perimetry: methods of threshold determination and comparison with visual responses," Perimtry Updated 1994/1994, pp. 119-123 (1994).

Katz, J. et al., "Repeatability of the Glaucoma Hemifield Test in automated perimetry," Invest. Opthalmol. Vis. Sci., pp. 1658-1664 (1995).

Krill, A., et al., "An absolute threshold defect in the inferior retina," Invest. Opthalmol., pp. 701-707 (1968).

Lachenmayr, B.J. et al., "Flicker perimtry resists rentinal image degradation," Invest. Opthalmol. Vis. Sci., pp. 3539-3542 (1992).

Lagreze, W.D. et al., "Correlation of relative afferent pupillary defect and estimated retinal ganglion cell loss," Graefes Arch. Clin. Exp. Opthalmol., pp. 401-404 (1998).

Levatin, P. "Pupillary escape in disease of the retina or optic nerve," Arch. Opthalmol., pp. 768-779 (1959).

Loewenfeld, I.E. et al., "Infrared pupil camera. A new method for mass screening and clinical use," Am. J. Opthalmol., pp. 304-313 (1974).

Lowenstein, O. et al., "The pupil as indicator of retinal activity," Am. J. Opthalmol., pp. 569-596 (1964).

Lowenstein, O. et al., "The Pupil," The Eye, pp. 255-337 (1969).

Lucas, R.J. et al., "Diminished pupillary light reflex at high irradiances in melanopsin-knockout mice," Science, pp. 245-247 (2003).

Maddess, T. et al., "Testing for glaucoma with the spatial frequency doubling illision," Vision Res., pp. 4258-4273 (1999).

Morgan, J.E. "Selective cell death in glaucoma: does it really occur?" Br. J. Opthalmol., pp. 875-879 (1994).

Newell, F.W. "The optic nerve," Opthalmol. Principles and Concepts, pp. 353-363 (1986).

Okuyama, S.M. et al., "Pupil perimetry with the Octopus 1-2-3," pp. 51-58 (1996).

Pearson, P. et al., "Chromatic and achromatic defects in patients with progressing glaucoma," Vision Res., pp. 1215-1227 (2001).

Pearson et al., "A method of sampling discrete ganglion cell mosaics which decreases threshold variability," Perimetry Update, pp. 111-117 (1998).

Perry, V.H. et al., "Retinal ganglion cells that project to the superior colliculus and pretectum in the macaque monkey," Neuroscience, pp. 1125-1137 (1984).

Quigley, H.A. et al., "Chronic human glaucoma causing selectively greater loss of large optic nerve fibers," Opthalmology, pp. 357-363 (1988).

Rodieck, R. "Informing the Brain," The first steps in seeing, pp. 276-279 (1998).

Sample, P.A., et al., "Asymmetries in the normal short-wavelength visual field: implications for short-wavelength automated perimetry," Am. J. Opthalmol., pp. 46-52 (1997).

Schweitzer, N.M.J. et al., "Differential threshold measurements on the light reflex of the human pupil," A.M.A. Arch. Opthalmol., pp. 541-550 (1957).

Skrandies, W. "The upper and lower visual field of Man: electrophysiological and functional differences," Sensory Physiology 8, pp. 48-93 (1987).

Spry, P.G. et al., "Variability components of standard automated perimetry and frequency-doubling technology perimetry," Invest. Opthalmol. Vis. Sci., pp. 1404-1410 (2001).

Stark, L. "Pupillary control system: its nonlinear adaptive and stochastic engineering design characteristics," Fed. Proc., pp. 52-64 (1969).

Swanson, W.H. et al., "Perimetric defects and ganglion cell damage: interpreting linear relations using a two-stage neural model," Invest. Opthalmol. Vis. Sci., pp. 466-472 (2004).

Thompson, H.S. "The Pupil," Adler's Physiology of the Eye, pp. 311-338 (1975).

Thompson, H.S. et al., "The relationship between visual acuity, pupillary defect, and visual field loss," Am. J. Opthalmol., pp. 681-688 (1982).

Trejo, L.J. et al., "Cells in the pretectal olivary nucleus are in the pathway for the direct light reflex of the pupil in the rat," Brain Res., pp. 49-62 (1984).

Tychsen, I. et al., "Relative afferent pupillary defect in congenital occipital hemianopia," Am. J. Opthalmol., pp. 345-346 (1985).

Tyler, C.W. "Specific deficits of flicker sensitivity in glaucoma and ocular hypertension," Invest. Opthalmol. Vis. Sci., pp. 204-212 (1981).

Ukai, K. "Spatial pattern as a stimulus to the pupillary system," J. Opt. Soc. Am. A., pp. 1094-1100 (1985).

Van Buren, J.M. "The retinal ganglion cell layer," Book (1963).

Vrabec, F. "The temporal raphe of the human retina," Am. J. Opthalmol., pp. 926-938 (1966).

Wall, J. et al., "Variability in patients with glaucomatous visual field damage is reduced using size V stimuli," Invest. Opthalmol. Vis. Sci., pp. 426-435 (1997).

Weber, J. et al., "The topographical relationship between optic disc and visual field in glaucoma," Acta. Opthalmol. (Copenh.), pp. 568-574 (1990).

Weber, J. et al., "The exact site of nerve fiber equivalent lines in the visual field," Fortschr. Opthalmol., pp. 101-103 (1987).

Weber, J. et al., "A perimetric nerve fiber bundle map," Int. Opthalmol., pp. 193-200 (1991).

Werner, E.B. et al., "Increased scatter of responses as a precursor of visual field changes in glaucoma," Can. J. Opthalmol., pp. 140-142 (1977).

Wild, J.M. et al., "Statistical aspects of the normal visual field in short-wavelength automated perimetry," Invest. Opthalmol. Vis. Sci., pp. 54-63 (1998).

Wilhelm, H. et al., "Pupil perimetry using M-sequence stimulation technique," Invest. Opthalmol. Vis. Sci., pp. 1229-1238 (2000).

Wyatt, H.J. "Clinical research note: a hypothesis concerning the relationship between retinotopy in the optic nerve head and perimetry," Clin. Vision Sci., 153-161 (1992).

Wyatt, H.J. et al., "Pupillary light reflex in humans: evidence for an unbalanced pathway from nasal retina, and for signal cancellation in brainstream," Vision Res., pp. 513-525 (1981).

Yoshitomi, T. et al., "Comparison of threshold visual perimetry and objective pupil perimetry in clinical patients," J. Neuroophthalmol., pp. 89-99 (1999).

Yoshiyama, K.K. et al., "Which method of flicker perimetry is most effective for detection of glaucomatous visual field loss?" Invest. Opthalmol. Vis. Sci., pp. 2270-2277 (1997).

Young, R.S. et al., "Transient and sustained components of the pupillary responses evoked by luminance and color," Vision Res., pp. 437-446 (1993).

Young, R.S. et al., "Transient and sustained components of the pupil response evoked by achromatic spatial patterns," Vision Res., pp. 2239-2252 (1993).

Asman, P. et al., "Evaluation of methods for automated Hemifield analysis in perimetry," Arch. Opthalmol., pp. 820-826 (1992).

Asman, P. et al., "Glaucoma Hernifield Test, Automated visual field evaluation," Arch. Opthalmol., pp. 812-819 (1992).

Aulhorn, E., et al., "Frequency distribution in early glaucomatous visual field defects," Documenta Opthalmological Proceedings Series: Second International Visual Field Symposium, pp. 75-83 (1976).

Berbie, H. "Computer-assisted evaluation of visual fields," Graefes Arch. Clin. Exp. Opthalmol., pp. 242-245 (1990).

Bell, R.A. et al., "Relative afferent pupillary defect in optic tract hemianopias," Am. J. Opthalmol., pp. 538-540 (1978).

Bouma, H. "Receptive Systems: mediating certain light reactions of the pupil of the human eye," Phillips Research Reports Supplements, pp. 112-160 (1965).

Bremmer, F.D. et al., "Comparing pupil function with visual function in patients with Leber's hereditary optic neuropathy," Invest. Ophthalmol. Vis. Sci., pp. 2528-2534 (1999).

Brown, R.H. et al., "The afferent pupillary defect in asymmetric glaucoma," Arch Opthalmol., pp. 1540-1543 (1987).

Casson, E.J. et al., "Longitudinal comparison of temporary-modulation perimetry with white-on-white and blue-on-yellow perimetry in ocular hypertension and early glaucoma," J. Opt. Soc. Am. A., pp. 1792-1806 (1993).

Chauhan, B.C. et al., "Test-retest variability of frequency-doubling perimetry and conventional perimetry in glaucoma patients and normal subjects," Invest. Opthalmol. Vis. Sci., pp. 648-656 (1999).

Chauhan, B. et al., "Characteristics of frequency-of-seeing curves in normal subjects, patients with suspected glaucoma, and patients with glaucoma," Invest. Opthalmol. Vis. Sci., pp. 3534-3540 (1993).

Clarke, R.J. et al., "Characteristics of the pupillary light reflex in the alert rhesus monkey," J. Neurophysiol., pp. 3179-3189 (2003).

Clarke, R.J. et al., "Preimate pupillary light reflex: receptive field characteristics of pretectal luminance neurons," J. Neurophysiol., pp. 3168-3178 (2003).

Curcio, C.A., et al., "Topography of ganglion cells in human retina," J. Comp. Neural., pp. 5-25 (1990).

Demirel, S. et al., "Isolation of short-wavelength sensitive mechanisms in normal and glaucomatous visual field regions," J. Glaucoma, pp. 63-73 (2000).

Drake, M.V. "Glaucomatous visual field loss," Principles and Practice of Opthalmology, pp. 1301-1310 (1994).

Frankhauser, F. et al., "Puptrak 1.0-a new semiautomated system for pupillometry with the Octopus perimeter: a preliminary report," Doc. Ophthalmol., pp. 235-248 (1989).

Felius, J.S., et al., "Spatial summation for selected ganglion cell mosaics in patients with glaucoma," Perimetry Update 1996/1997, pp. 213-221 (1996).

Flammer, J. et al., "Differential light threshold. Short-and long-term fluctuation in patients with glaucoma, normal controls, and patients with suspected glaucoma," Arch. Opthalmol., pp. 704-706 (1984).

Gamlin, P.D. et al., "Luminance neurons in the pretectal olivary nucleus mediate the pupillary light reflex in the rhesus monkey," Exp. Brain Res., pp. 169-176 (1995).

Garyway-Heath, D.F. et al., "Scaling the hill of vision: the physiological relationship between light sensitivity and ganglion cell numbers," Invest. Opthalmol. Vis. Sci., pp. 1774-1782 (2000).

Garyway-Heath, D.F. et al., "Mapping the visual field to the optic disc in normal tension glaucoma eyes," Opthalmology, pp. 1809-1815 (2000).

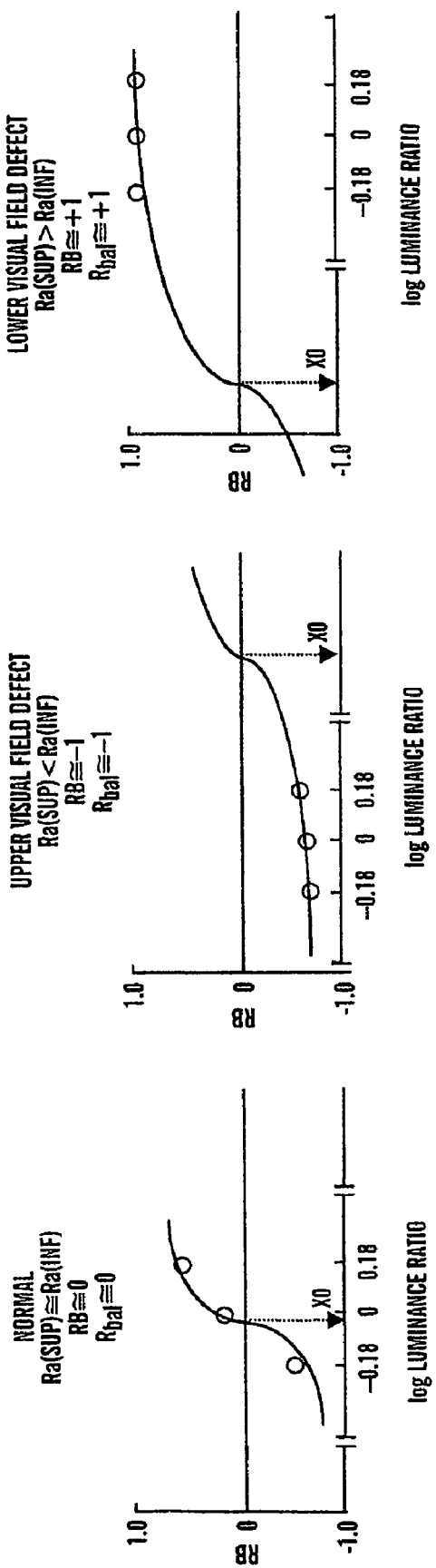

APPARATUS AND METHOD FOR ASSESSING RETINAL DAMAGE

RELATED APPLICATION

This application is a divisional of U.S. patent application Ser. No. now 10/972,613, filed Oct. 25, 2004, which claims the benefit of U.S. Provisional Application No. 60/551,649 filed on Mar. 9, 2004, both of which are incorporated herein by reference in their entirety.

BACKGROUND OF THE INVENTION

1. Technical Field

The present invention generally relates to an apparatus and method for assessing retinal damage to an eye and in particular to an apparatus and method for assessing glaucomatous retinal damage to an eye.

2. Related Art 2.1 Glaucoma Epidemiology

Glaucoma is the second most common cause of blindness in the United States, and the single most important cause of blindness among black Americans. About 80,000 Americans are blind from primary open-angle glaucoma ("POAG"). At least 2 million Americans have POAG, but about half are unaware of it. About 5 to 10 million Americans are ocular hypertensives having an elevated intraocular pressure ("IOP") that places them at increased risk for the development of POAG. The rate at which such ocular hypertensives develop POAG is about 5 to 10 cases per thousand per year, an incidence which increases with age and the level of the IOP.

2.2. Glaucoma Clinical Indicia

Glaucoma refers to a group of diseases of unknown etiology, whose clinical features generally include [i] atrophy of the optic nerve head, [i] visual field defects, and [iii] an elevation in IOP. An elevation in IOP is not a universal feature of glaucoma. Atrophy of the optic nerve head and visual field defects may arise in the setting of an IOP that is within normal limits. This situation obtains in the case of, for example, normotensive glaucoma. Glaucomatous optic nerve head atrophy is generally detected with an opthalmoscope. Glaucomatous visual field defects are generally detected and mapped with a perimeter, and elevations in IOP are generally measured with an applanation tonometer or like device.

2.3 Optic Nerve Head

Using an opthalmoscope, the normal optic nerve head appears as a vertically oriented oval structure in the posterior retina within which a yellow-hued depression, called the optic cup, may be distinguished from a pink-hued neuroretinal rim, and from which retinal vessels course into the retina.

About 1.2 million retinal nerve fibers—axons arising from retinal ganglion cells—are gathered at the optic nerve head to form the optic nerve, which emerges from the back of the eye and extends to the brain. Simplistically, the optic nerve head may be regarded as an anterior axial section through a tube of neural cables that carry the modulated input of the retina used by the brain to create the sense of vision.

2.4 Optic Nerve Head Changes in Glaucoma

Ophthalmoscopic changes in the optic nerve head associated with glaucoma include enlargement, distortion, pallor or deepening of the optic cup, thinning of the neuroretinal rim, the emergence of splinter hemorrhages, and changes in the morphology of retinal blood vessels. These changes are associated with atrophy, scarring and loss of retinal nerve fibers.

2.5 Distinguishing the Visual Field from Visual Acuity

In discussing glaucoma it is important to distinguish visual acuity from the visual field. As an approximation, an eye's visual acuity refers to how sharply it brings things in the world into focus, whereas an eye's visual field refers to how much of the world is seen. Alternatively stated, the visual field refers to the entire area of space that is visualized by an eye while its gaze is fixed.

It possible for an individual to have very keen visual acuity that is limited to a narrow visual field, or a partial visual field outside of which the world does not exist visually. This visual state may be simulated by having a person with normal visual acuity gaze through a narrow pipe or hold a finger over the upper eyelid so that it occludes the superior visual field.

Because glaucoma leads to destruction of retinal nerve fibers carrying the modulated output of retinal photoreceptor cells (as opposed to destruction of the lens or cornea, which form the refractive media of the eye), glaucoma is primarily destructive of a patient's visual fields. Consequently, the detection and mapping of the visual field of each eye is important to the diagnosis and management of glaucoma.

2.6 Visual Field Perimetry

The most widely used technique for assessing glaucomatous damage is subjective visual field testing or perimetry. In perimetry, a patient is seated facing the opening of a hollow hemispheric bowl whose central axis is oriented horizontally. The patient's chin is supported by a chin rest. A constellation of small light sources of variable luminance is arrayed over the inner surface of the hemisphere. One of the patient's eyes is occluded and a trial lens correcting the patient's refractive error is placed in front of the eye to be tested. The patient is instructed to direct the gaze of the open eye onto a fixation target centered at the pole of the hemisphere opposite his or her line of sight, and is further instructed not to allow his or her gaze to drift from the fixation target, relying entirely on peripheral vision to respond to the test. The test is conducted by illuminating the small light sources arrayed across the inner surface of the hemisphere in any of a number of predetermined test strategies. The patient is instructed to press a button on a hand-held device whenever a light flash is discerned anywhere in the field of vision except at the fixation point. The patient's responses are recorded and mapped as a grayscale image depicting visual sensitivities of the retina in shades of gray. Areas of very poor retinal sensitivity are darkly shaded, and areas of good retinal sensitivity are lightly shaded.

Conventional perimetry requires the presence of an operator, and has largely been supplanted by automated perimetry, in which the role of the operator has been assumed by a computer.

2.7 Threshold Strategies

Automated perimeters employ predetermined strategies to test the visual field. Since it is impractical to test every point in the visual field, each strategy uses a grid of test points that covers a circular central area of the visual field that is most likely to show glaucomatous defects. Each point in the grid is tested to determine the visual sensitivity of the central retina to a light stimulus. Just as it is not practical to test each point in the visual field, it is not practical to test any given point in the grid with a wide range of stimulus intensities. Accordingly, threshold strategies have been developed to define a standard level of sensitivity and to find that level with the smallest number of trials.

A stimulus that is bright enough to be easily seen should elicit a response from a patient 100% of time. A stimulus that is too dim to be seen should never elicit a response. Some-where between there should be a stimulus intensity that will elicit a response from a patient in half of the presentations; and the threshold is defined as that level of light intensity to which a patient responds 100% of the time.

If a stimulus is above (brighter than) the threshold level, it is said to be suprathreshold. If a stimulus is below (dimmer than) the threshold level it is said to be infrathreshold. The threshold stimulus for a point on the retina is determined by exposing it to stimuli above and below a presumptive threshold value in a process called bracketing. The presumptive threshold value is derived from known age-dependent normal values obtained from population studies.

If a first stimulus presentation is suprathreshold, then the computer presents the next stimulus at a level that is, for example, 4 dB lower. If the second stimulus elicits a response, then the computer lowers the stimulus level once again, for example, by 4 dB. This lowering of the stimulus level continues until the stimulus no longer elicits a response, indicating that the threshold has been crossed, and that an infrathreshold stimulus level has been found. The next stimulus is then raised, for example, by 2 dB. If the stimulus elicits no response, then the next stimulus is raised again, for example, by 2 dB. This process continues until the stimulus once again elicits a response in the patient's suprathreshold zone.

Accordingly, the threshold is crossed twice. After the second crossing has occurred, the search is terminated. The threshold value then lies between the visualized suprathreshold stimulus having the lowest intensity and the nonvisualized infrathreshold stimulus having the highest intensity.

2.8 Screening Strategies

Automated perimeter screening strategies are designed to quickly determine whether a significant visual defect is present. If a defect is detected, then a more comprehensive threshold strategy is used to characterize the defect.

Screening strategies use known normal threshold values to present only suprathreshold stimuli that are just above the normal threshold values. If the patient misses a significant number of these stimuli, then the automated perimeter is considered to have detected a defect that warrants further testing.

2.9 Disadvantages of Perimetry

Automated perimetry is beset with a number of disadvantages arising from the subjectivity of the patients' responses and the excessive duration of the test. Patients dislike the test because it is long and tedious. Measurement of the visual field of one eye can take about 10 to 20 minutes. Test anxiety, attention deficits, fatigue and boredom interfere with perimetry in both the young and the elderly. A desire to influence the outcome of the test favorably can result in false positives (pressing the button to signal visualization of a light stimulus when no light has been activated). Attention deficits can result in false negatives (failing to press the button to signal visualization of a light stimulus having a suprathreshold luminance). The results of automated perimetry are often unreliable.

Stimulating a larger retinal area in perimetry with a single large-area light stimulus, instead of using point stimuli, would reduce the duration of perimetry testing. However, the patient's response to a larger-area threshold test in perimetry may be mediated by undamaged retinal areas near damaged retinal areas. In such a case, a patient may see only a portion of the large-area stimulus, but still offer a response that will be falsely indicative of visualization of the entire stimulus. Thus, a large-area threshold test in perimetry is likely to be associated with a substantial risk of a falsely normal test result.

2.10 Pupillary Light Reflex: PLR

The pupillary light reflex ("PLR") is a clinical sign of the condition of the central nervous system ("CNS"). In a normal patient, exposure of the pupil of one eye to a light stimulus results in a symmetric constriction of both pupils.

2.11 Pupil Perimetry

A quantitative measurement of a PLR may be obtained using an instrument called a pupillometer.

Pupil perimetry usually employs a pupillometer together with a stimulus arrangement similar to that of a perimeter. However, instead of measuring the visual responses to incremental increases over a threshold in the intensity of a light stimulus, pupil perimetry measures the latency and amplitude of the constriction of the pupil in response to a spot ("small-area") stimulus, with a fixed suprathreshold luminance, that is directed to different locations on the retina.

The pupillary response to spatially-localized luminance increments has been used as an indicator of glaucomatous retinal damage, but the small-area stimuli used in pupil perimetry may target small retinal areas that only weakly stimulate a PLR, and may fail to stimulate a PLR if the small retinal area that is being stimulated by light has been damaged by glaucoma. Large variations in pupil response amplitude among patients and the changes in sensitivity of the pupil response with the retinal location of the small-area light stimulus have also limited the usefulness of such measurements. Additionally, prevailing pupil perimetry takes a relatively long time to perform.

A faster pupil perimetric exam is desirable, especially for purposes of screening large populations for glaucoma.

There is a need for an objective and rapid technology for assessing glaucomatous damage that is not beset with the disadvantages of either pupil perimetry or visual field perimetry.

SUMMARY OF THE INVENTION

The present invention comprises an apparatus and method for objectively measuring the visual sensitivity of a superior retina and the visual sensitivity of an inferior retina in an eye, comprising at least one computing device operationally connected to at least one stimulus presentation device, at least one pupil display device, at least one input device, at least one operator display device, at least one pupillometer, operational software, and data analysis software, wherein the stimulus presentation device presents at least one stimulus test with respect to which the computing device computes a pupillary response curve.

The present invention rapidly and objectively detects the presence of retinal nerve fiber damage, and rapidly and objectively assesses the progress of previously diagnosed retinal nerve fiber damage.

The present invention rapidly and objectively detects the presence of glaucoma, and rapidly and objectively assesses the progress of glaucoma in previously diagnosed cases.

The stimulus test presented by the present invention is far less tiring for patients being tested because they not have to make subjective judgments about visualizing stimuli and do not have to consciously respond during the test.

BRIEF DESCRIPTION OF THE DRAWINGS

FIG. 16a shows an exemplary graph of the pupillary response balances of a normal patient fitted to a sigmoid function of the luminance ratios (in log units) associated with that patient's pupillary response balances.

FIG. 16b shows an exemplary graph of the pupillary response balances of a patient with a superior visual field defect fitted to a sigmoid function of the luminance ratios (in log units) associated with mat patient's pupillary response balances.

FIG. 16c shows an exemplary graph of the pupillary response balances of a patient with an inferior visual field defect fitted to a sigmoid function of the luminance ratios (in log units) associated with that patient's pupillary response balances.

DETAILED DESCRIPTION OF THE INVENTION

3.1 Glaucoma

As used herein the term glaucoma comprises all pathophysiological states of the human eye presenting with an elevation in IOP and either a visual field defect or optic atrophy, and includes but is not limited to acute angle-closure glaucoma, angle-recession glaucoma, drug-induced glaucoma, hemolytic glaucoma, hemosiderotic glaucoma, juvenile glaucoma, low-tension glaucoma, malignant glaucoma, narrow-angle glaucoma, neovascular glaucoma, normotensive glaucoma, phacolytic glaucoma, phacomorphic glaucoma, pigmentary glaucoma post-surgical glaucoma, primary open-angle glaucoma, primary infantile glaucoma, pseudoexfoliative glaucoma, pupillary block glaucoma uveitic glaucoma, aniridia, aqueous misdirection syndrome, irido-corneal-endothelial syndrome and plateau iris syndrome.

3.2 Ocular Anatomy

Figure 1:
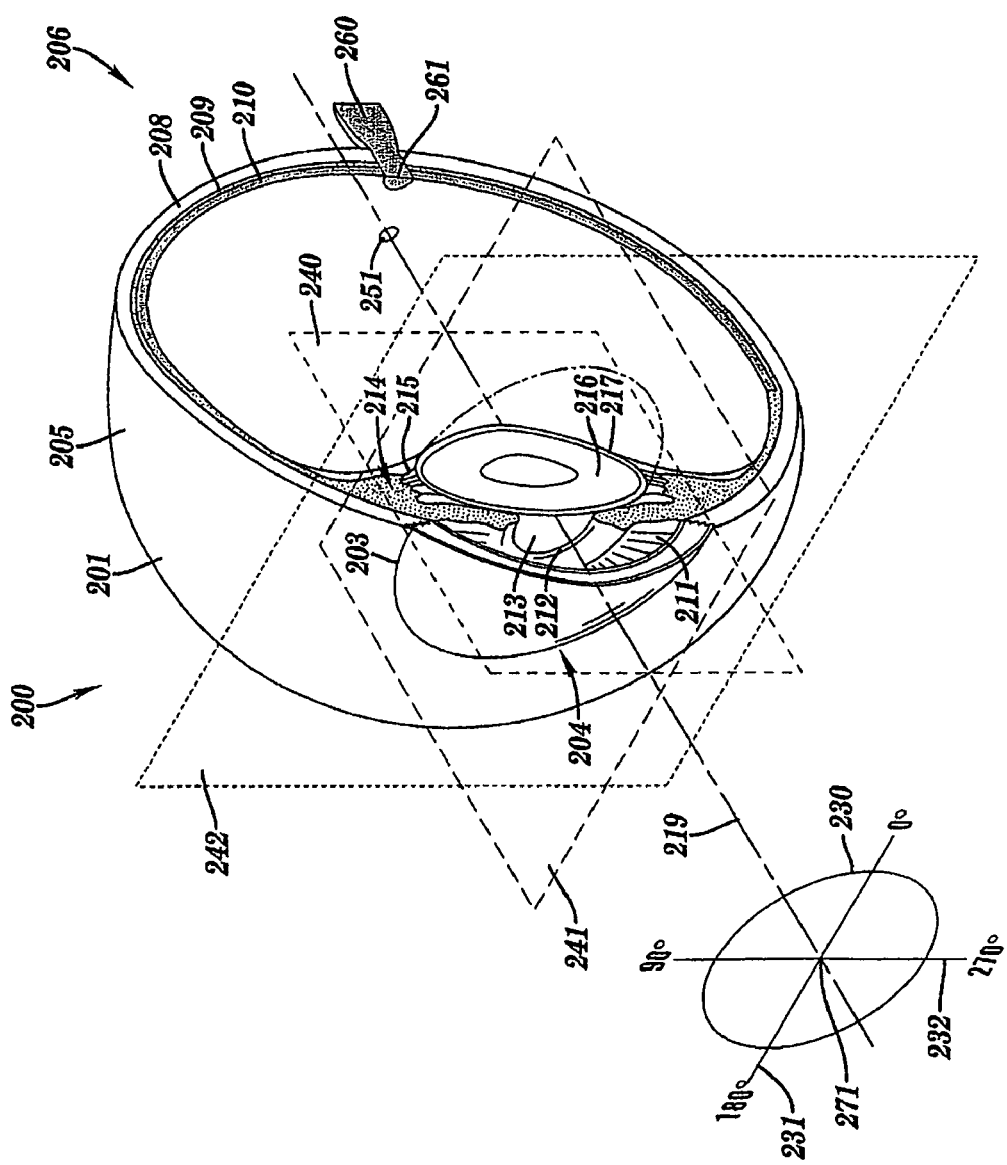
FIG. 1 shows a schematic perspective illustration of a human eye.

FIG. 1 is a schematic perspective illustration of a human eye 200, set against an anatomical sagittal plane 240, an anatomical axial plane 241 and an anatomical coronal plane 242.

The shape of the human eye may generally be regarded as formed by the intersection of a first larger ("scleral") sphere 201 with a second ("corneal") smaller sphere (not shown in FIG. 1), the visible portion of which protrudes from first sphere 201 as the anterior convexity of the eye—the transparent cornea 204. The generally circular line of intersection of these spheres forms the limbus 203, a line of demarcation that circumscribes cornea 204. The larger second sphere 201 of the eye 200 posterior to limbus 203 forms the white shell of the eye 205, whose posterior aspect is pierced by the optic nerve 260.

The shell of the eye 205 is a tri-lamellar tissue, having an outermost fibrous layer known as the sclera 208, a middle vascular layer known as the choroid 209, and an innermost photosensitive layer, known as the retina 210. The most discriminatingly photosensitive region of the retina is confined to a region called the macula 251. The optic nerve 260 enters the eye and appears on the retina 210 as the optic nerve head 261 nasal to the macula 251 of eye 200.

Projecting radially inward from the shell 205 of the eye 200 and circumferentially adjacent the limbus 203 is a circular diaphragm of tissue known as the iris 211, whose innermost circular border forms the margin 212 of an aperture called the pupil 213. Immediately posterior and continuous with the iris 211 is the muscular ciliary body 214, from which there are circumferentially elaborated a plurality of strands, called zonules 215, projecting radially inward to tether the crystalline lens 216 just posterior to iris 211. Zonules 215 insert onto a lens capsule 217 that envelopes the crystalline lens 216.

3.3 Retinal Anatomy

Figure 2:
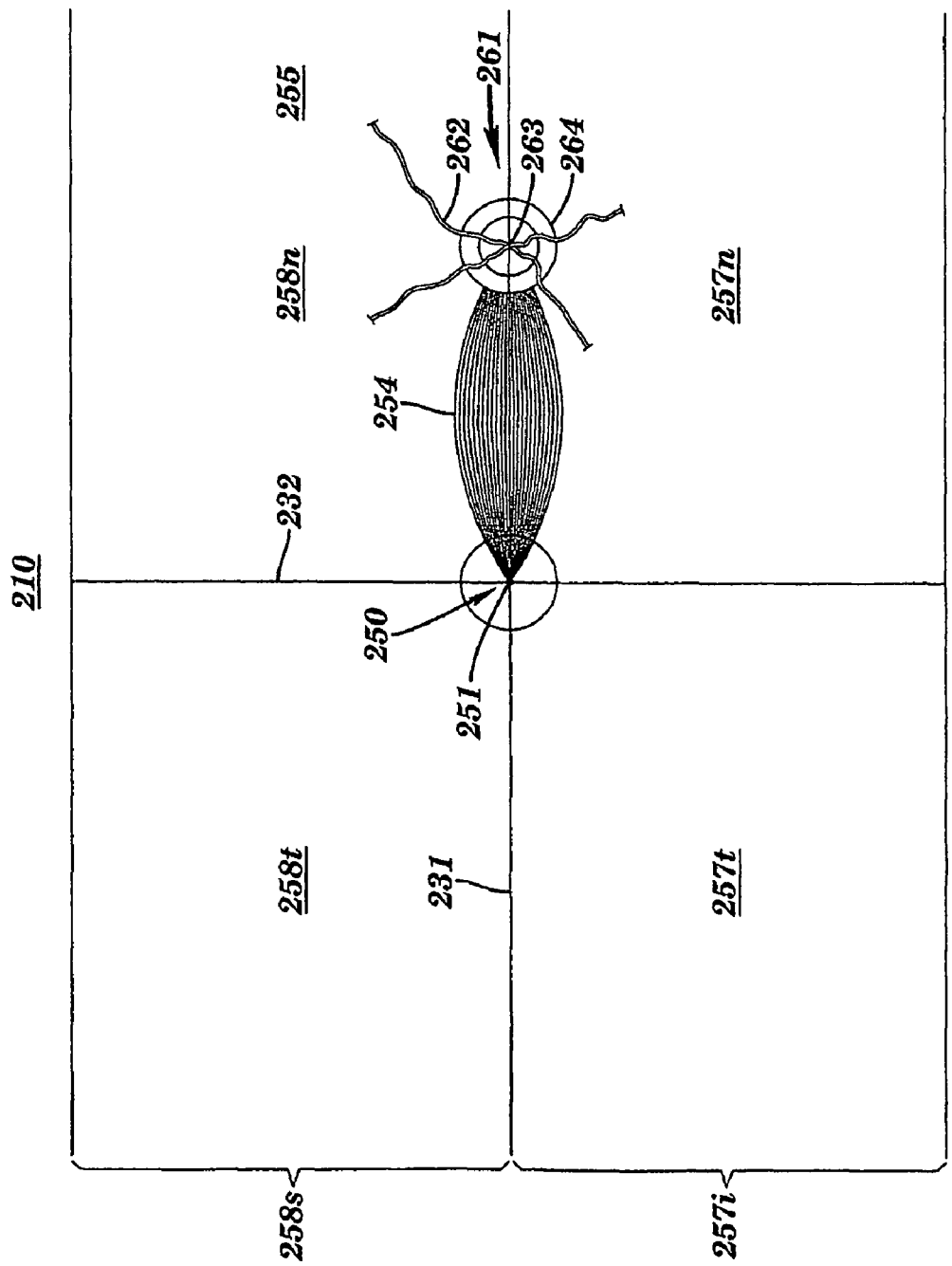
FIG. 2 shows a schematic planar illustration of the posterior retina.

FIG. 2 shows a paracentral portion of retina 210 of FIG. 1 in greater detail. The retina is comprised of a central retina 250 and a peripheral retina 255. The central retina 250 refers to that region of the retina circumscribed by the macula 251. The choroid 209, ciliary body 214, and iris 211 are conjunctively referred to as the uvea.

The retina beyond the macula 251 is called the peripheral retina 255. The peripheral retina terminates at the ora serrata (not shown in FIG. 1 or FIG. 2), a circumferential anatomic landmark just posterior to the ciliary body 214 of the eye 200 (FIG. 1).

3.4 Optic Nerve Anatomy

As shown in FIG. 2, the optic nerve head ("ONH") 261 is the site of the elaboration of retinal blood vessels 262. When viewed with an opthalmoscope, the ONH is comprised of a depression or optic cup 263 of variable depth and contour that is circumscribed by a rim of tissue called the neuroretinal rim 264.

The ratio of the vertical diameter of the optic cup to the vertical diameter of the ONH is called the cup-to-disc ratio. The cup-to-disc ratio is used by clinicians as a semi-quantitative index of glaucomatous damage to the ONH. A nonglaucomatous eye will generally have a cup-to-disc ratio of about 1/3. The cup-to-disc ratio generally increases with increasing glaucomatous damage to the ONH, reflecting an erosion of the neuroretinal rim.

3.5 Retinal Nerve Fibers

Figure 3:
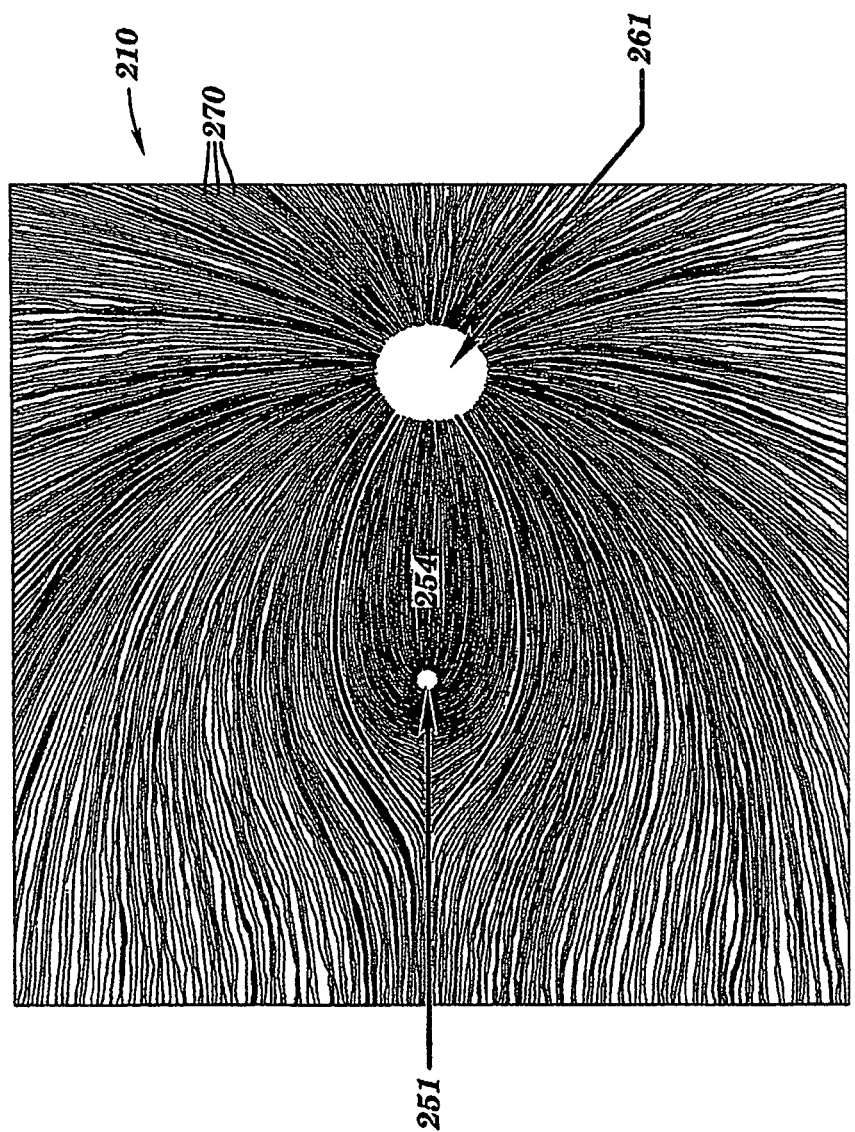
FIG. 3 shows the arrangement of the retinal nerve fibers in the nerve fiber layer of the retina.

FIG. 3 is a schematic illustration of the pattern of distribution of retinal nerve fibers 270 in a retina 210. In FIG. 3, a relatively well-defined elliptical bundle of retinal nerve fibers connects the macula 251 to the optic nerve head 261, and is referred to as the papillomacular bundle 254.

3.6 Correlation of Visual Field Scotomas with Retinal Nerve Fiber Damage

Figure 4:
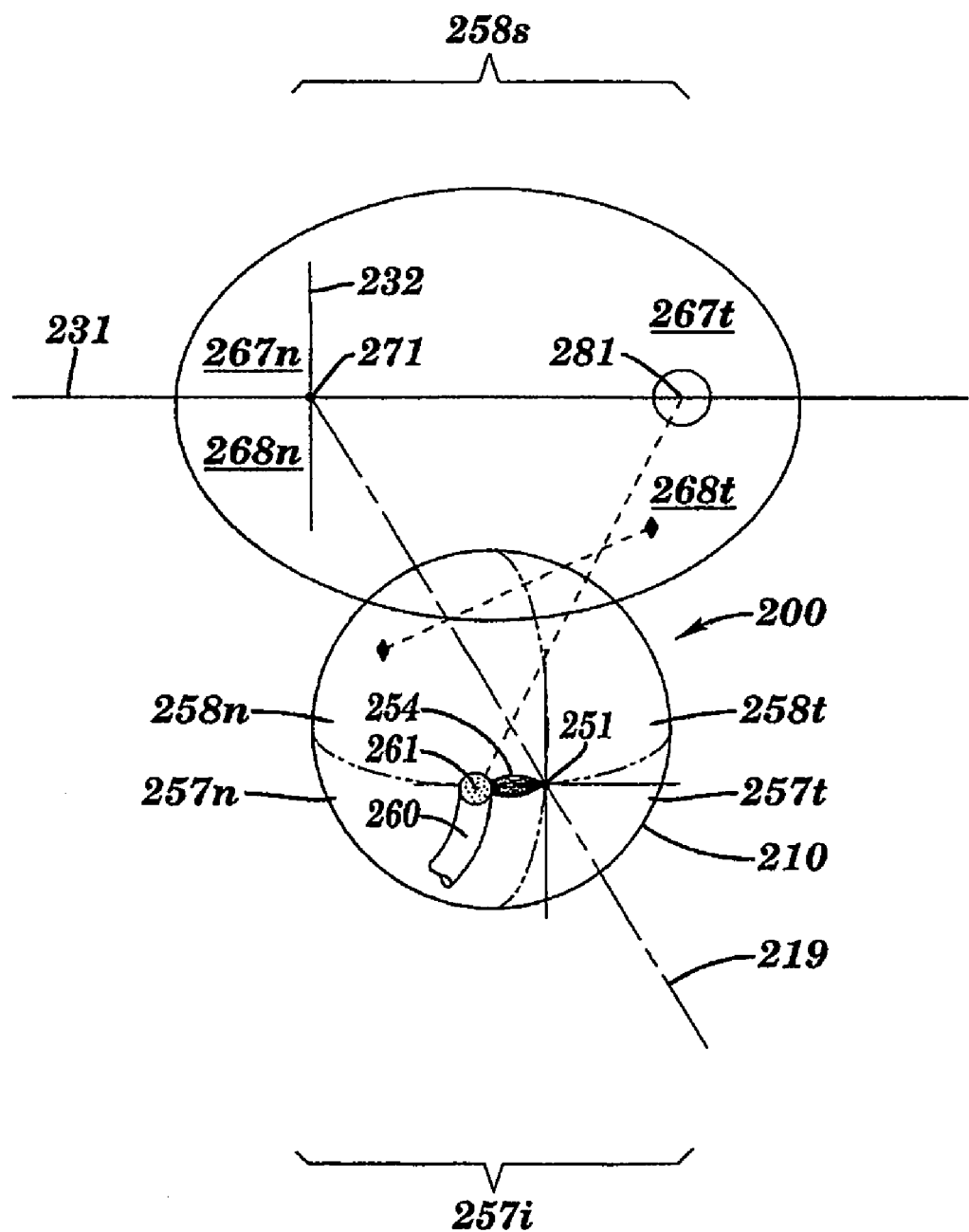
FIG. 4 is a schematic illustration of a right eye viewed from behind with its visual field projected anteriorly.
Figure 5:
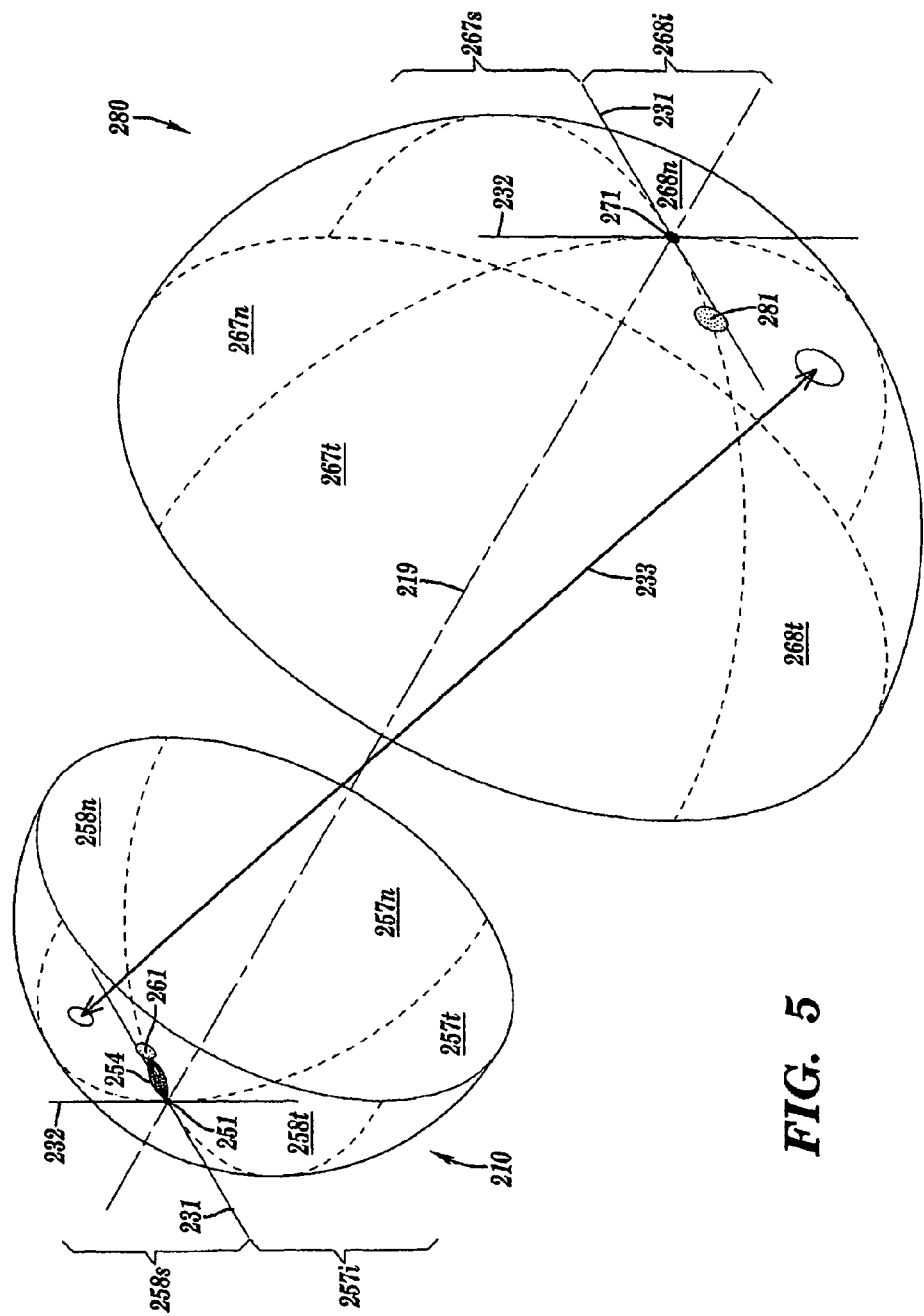
FIG. 5 is a schematic perspective illustration of the correspondence between anatomic portions of a retina of a right eye and its visual field.

FIG. 4 is a schematic illustration of a right eye viewed from behind with its visual field projected anteriorly. FIG. 5 is a schematic perspective illustration showing the correspondence between anatomic portions of the retina of a right eye and its visual field.

As shown in FIG. 4, orientation about eye 200, its retina 210, and the projection of retina 210 onto the visual field of eye 200 is determined by reference to horizontal meridian 231 and vertical meridian 232. Horizontal meridian 231 and vertical meridian 232 also appear in reference plane 230 parallel to coronal plane 242 in FIG. 1, and in FIG. 2.

Horizontal meridian 231 and vertical meridian 232 are orthogonal and intersect at the visual axis 219 of eye 200 (FIG. 1 and FIG. 4). In FIG. 1, visual axis 219 extends from the macula 251 anteriorward, approximately perpendicular to coronal plane 242, approximately along sagittal plane 240, and through cornea 204. The intersection of visual axis 219 with a plane, such as, for example, reference plane 230 of FIG. 1 or any plane onto which the visual field of retina 210 is mapped is called the fixation point 271 (FIG. 1 and FIG. 4).

As shown in FIG. 2, FIG. 4 and FIG. 5, the retina 210 may be conveniently divided into quadrants defined by horizontal meridian 231, and vertical meridian 232, crossing at macula 251 (or fixation point 271). The superior nasal quadrant 258n and the superior temporal quadrant 258t form the superior retina 258S. The inferior nasal quadrant 257n and the inferior temporal quadrant 257t form the inferior retina 257I.

Glaucomatous damage is often asymmetric with respect to horizontal meridian 231, so that inferior retina 257I and superior retina 258S may be afflicted to substantially different degrees. However, glaucoma may also be associated with a diffuse loss or generalized depression of the visual field, that effects inferior retina 257I and superior retina 258S to about the same extent.

Visual sensitivity of the retina to light is reflectively correlated with the visual field and glaucomatous retinal nerve damage is reflectively correlated with visual field defects. As show in FIG. 4 and FIG. 5, both correlations are geometrically diagonalized. For example, as shown by double-headed arrow 233 in FIG. 5, retinal nerve fiber damage in superior nasal quadrant 258n of the retina 210 will give rise to a visual field defect in the inferotemporal visual field 268t. As shown in FIG. 5, the projection of the macula 251 onto the visual field 280 identifies the fixation point 271 of the eye.

The key correlations between retinal regions and anatomic landmarks of retina 210 in FIG. 5 and the visual field 280 of retina 210 in FIG. 5 are summarized in TABLE 1.

TABLE 1

Correlation Between Retinal Regions and Landmarks and the Visual Field

| Retinal Region 210 | Reference Numeral | Visual Field 280 | Reference Numeral |
| --- | --- | --- | --- |
| inferonasal quadrant | 257n | superotemporal field | 267t |
| Inferotemporal quadrant | 257t | superonasal field | 267n |
| inferior hemiretina | 257i | superior hemifield | 267s |
| superonasal quadrant | 258n | inferotemporal field | 268t |
| superotemporal quadrant | 258t | inferonasal field | 268n |
| superior hemiretina | 258S | inferior hemifield | 268I |
| macula | 251 | fixation point | 271 |
| optic nerve head | 261 | blind spot | 281 |

3.7 Proximity to Fixation

Figure 6:
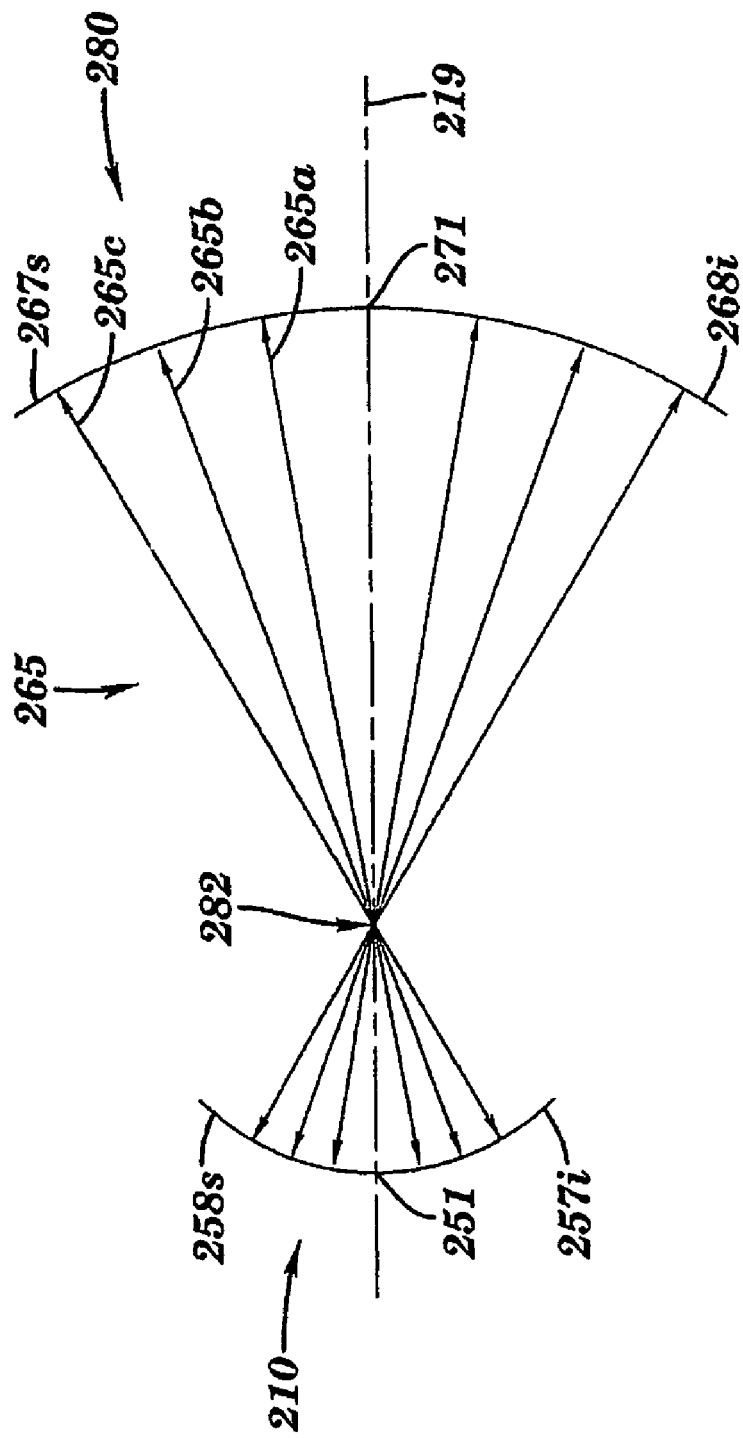
FIG. 6 is a schematic illustration of the correspondence between points on the retina and points on the visual field at the intersection of the retina and the visual field with an anatomical sagittal plane.

FIG. 6 is a schematic illustration of the correspondence between points on the retina and points on the visual field at the intersection of the retina and the visual field with anatomical sagittal plane 240 (FIG. 1). As shown in FIG. 6, each point of the retina 210 has a corresponding "conjugate" point on the visual field 280. Conjugate points may joined by "conjugate lines, shown in FIG. 6 as double-headed arrows 265, that pass through an effective center 282 of the eye's optics, lying within crystalline lens 216 of eye 200 (FIG. 1).

As shown in FIG. 6, macula 251 on retina 210 and fixation point 271 on visual field 280 are joined by visual axis 219, which is also a conjugate line. Proximity to either macula 251 or fixation point 271 is measured by reference to conjugate lines 265, such as, for example, conjugate line 265a, corresponding to 10 degrees, conjugate line 265b, corresponding to 20 degrees, and conjugate line 265c, corresponding to 30 degrees.

Points within 10 degrees of fixation are closer to the fixation point 271 than are points between 20 and 30 degrees of fixation. Points within 10 degrees of macula 251 are closer to the macula 271 than are points between 20 and 30 degrees of fixation.

The optic nerve head 261 (FIG. 5) contains no photoreceptor cells. Consequently, the projection of the contour of the optic nerve head onto the visual field of the eye outlines the perimeter of a natural blind spot 281 (FIG. 5) that is present in the visual fields of all humans.

3.8 Normal Clinical Values

The interpretation of a measured or computed clinical parameter entails comparing the measured or computed clinical parameter obtained from an individual patient to a measured or computed clinical parameter obtained from a large population of normal patients ("normative data"). A plot of the frequency with which the value of a measured or computed clinical parameter is obtained from a population against the values of the measured or computed clinical parameter often assumes the bell-shaped form of a classical "normal" or Gaussian distribution, in which the mean represents the average value of the measured or computed clinical parameter in the population and the standard deviation is a measure of the spread of the measured or computed clinical parameter about the mean.

If a clinical measurement is obtained from an individual patient, such as, for example, a measurement of the IOP, or if a clinical computation is made for a patient, such as, for example, the computation of a visual field defect, then a determination of whether the measurement or computation is normal is generally made by reference to a corresponding normal distribution. Generally an individual clinical measurement or computation is regarded as abnormal if it falls beyond a certain multiple of the standard deviation for the corresponding normal distribution.

Generally, the further an individual clinical measurement or computation is from the mean for the clinical measurement or computation, the less likely it is that the individual clinical measurement or computation represents a normal value. For example, if a clinical measurement of computation is about two standard deviations away from a mean normal value, there is only a very small (e.g., 2.5%-5%) chance that the clinical measurement or computation represents a normal value. If a clinical measurement of computation is about three standard deviations away from a mean normal value there is only an exceedingly small (e.g., 0.125%-0.25%) chance that the clinical measurement or computation represents a normal value.

3.9 Glaucomatous Visual Field Defects

The correlation of visual field defects with glaucomatous damage to retinal nerve fibers has resulted in the observation that glaucoma is associated with a plurality of visual field defects ("scotomas") having identifiable topographical characteristics. Among the more common visual field defects associated with, for example, primary open-angle glaucoma are: [i] a paracentral scotoma; [ii] a Bjerrum's scotoma; and a [iii] a nasal peripheral scotoma. Other visual field defects that may be associated with glaucoma include: [i] a central scotoma that implicates the macula; [ii] a centrocecal scotoma that incorporates the optic nerve head; [iii] (rarely) an altitudinal scotoma that involves two quadrants in the superior or inferior retina; and [iv] a generalized depression of the visual field ("diffuse visual field loss").

Figure 7A:
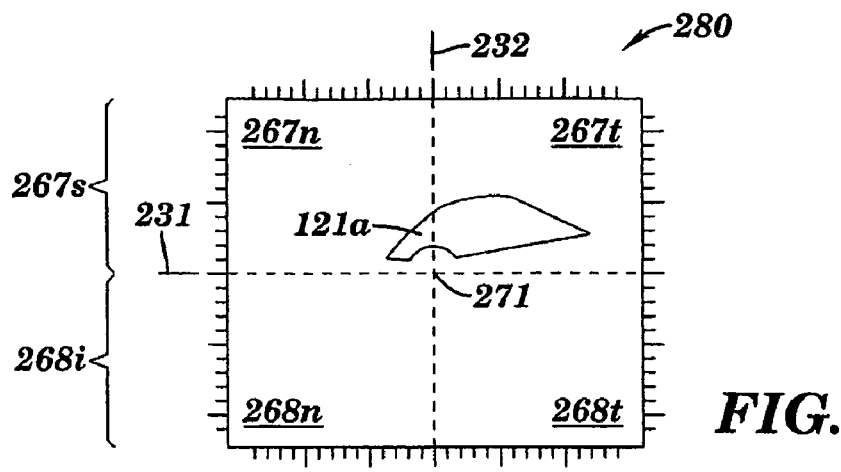
FIG. 7a is a schematic illustration of an exemplary superior retinal region bounding visual field losses conforming to a paracentral scotoma in the visual field of a right eye.

FIG. 7*a* is a schematic illustration of an exemplary superior retinal region bounding visual field losses conforming to a paracentral scotoma in the visual field of a right eye. Superior paracentral scotoma 121*a* is near to the fixation point 271, and typically reflects glaucomatous damage near the macula 251 and the papillomacular bundle 254 (FIG. 2, FIG. 4 and FIG. 5).

Figure 7B:
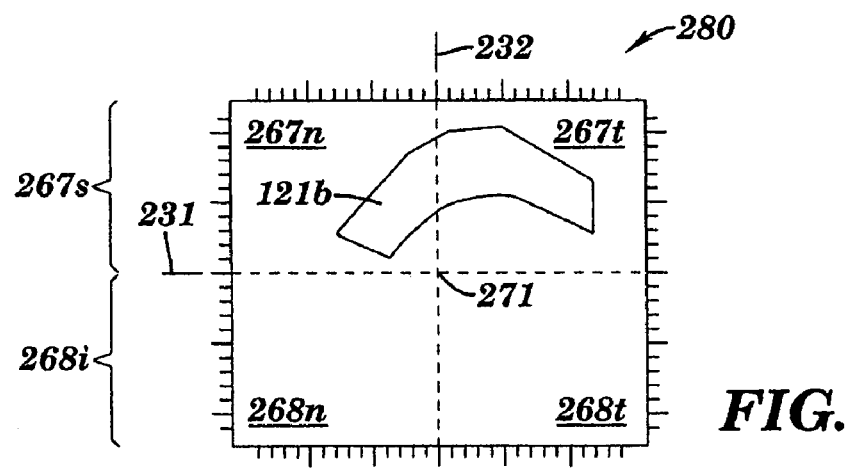
FIG. 7b is a schematic illustration of an exemplary superior retinal region bounding visual field losses conforming to a Bjerrum's scotoma in the visual field of a right eye.

FIG. 7*b* is a schematic illustration of an exemplary superior retinal region bounding visual field losses conforming to a Bjerrum's scotoma in the visual field of a right eye. A Bjerrum's scotoma is a classic form of an arcuate scotoma corresponding to the loss of a retinal nerve fiber bundle along a wedge or arch of the retina, typically within 10 to 20 degrees of fixation point 271.

Figure 7C:
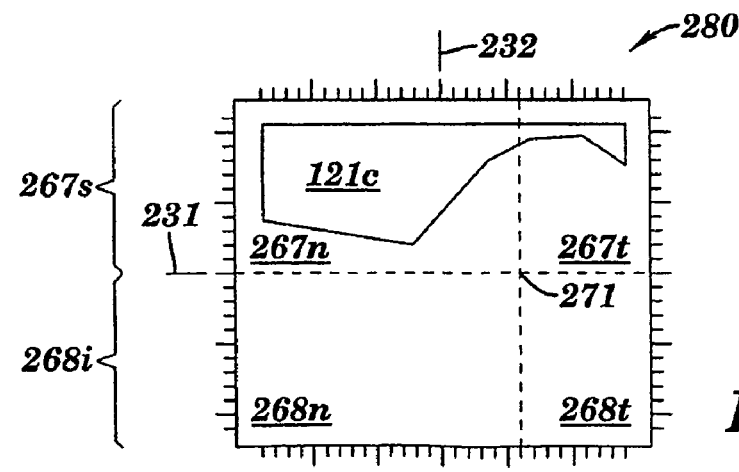
FIG. 7c is a schematic illustration of an exemplary superior retinal region bounding visual field losses conforming to a peripheral scotoma in the visual field of a right eye.

FIG. 7*c* is a schematic illustration of an exemplary superior retinal region bounding visual field losses conforming to a peripheral scotoma in the visual field of a right eye. A peripheral scotoma spares the macula 251 and the papillomacular bundle 254 (FIG. 2, FIG. 3, FIG. 4, FIG. 5), affecting only peripheral vision.

3.10 Introduction: Functions of the Invention

The invention objectively measures the visual sensitivity of the superior retina and the visual sensitivity of the inferior retina ("horizontally paired retinal areas") of the same eye, by computing time-dependent changes in the diameter of the eye's pupil ("pupillary response curve") that are responsive to a stimulus test presented by the invention. The stimulus test alternately presents a shaped superior light stimulus ("shaped superior stimulus") to the superior retina and a shaped inferior light stimulus ("shaped inferior stimulus") to the inferior retina, which shaped superior and inferior light stimuli are mirror images of one another with respect to the horizontal meridian 231 (FIG. 1, FIG. 2, FIG. 4, FIG. 5), and have shapes encompassing and corresponding to visual field defects, such as, for example, visual field defects that are characteristic of glaucoma, including a central scotoma, a paracentral scotoma, an altitudinal scotoma, a Bjerrum's scotoma, a peripheral scotoma, a nasal step, an arcuate scotoma and a generalized depression of the visual field.

In the present invention, a shaped superior or inferior stimulus is characterized by a selectable shape, area, luminance, and presentation time.

3.11 Organization of Stimulus Presentations

3.11a Stimulus Pair

The alternate presentation by the invention to the eye of a patient of a shaped superior light stimulus and its mirror image shaped inferior light stimulus in any order comprises the presentation of a stimulus pair—in effect the "unit" of stimulus presentation to the eye of patient. However, in certain applications of the invention, a stimulus pair may be selectably divided to present only its constituent shaped superior stimulus or its constituent shaped inferior stimulus.

The alternate presentation of a shaped superior light stimulus and its mirror image shaped inferior light stimulus respectively stimulate a corresponding superior retinal pupillary response and a corresponding inferior retinal pupillary response, whose amplitudes of constriction are measured by the invention.

A single presentation by the invention of a single stimulus pair comprises the presentation of one shaped superior stimulus that lasts for a superior stimulus presentation time followed by the presentation of one shaped inferior stimulus that lasts for a inferior stimulus presentation time; or, alternatively, the presentation of one shaped inferior light stimulus that lasts for an inferior stimulus presentation time followed by the presentation of one shaped superior stimulus that lasts for a superior stimulus presentation time.

A single presentation of one stimulus pair by the invention lasts for a stimulus pair presentation time that is equal to the sum of an inferior stimulus presentation time and a superior stimulus presentation time.

3.11b Stimulus Cycle

The presentation to the eye of a patient of a selectable number (one or more) stimulus pairs whose constituent superior and inferior stimuli have the same shape comprises the presentation of a stimulus cycle.

A stimulus cycle may, for example, be comprised of the presentation of 3 stimulus pairs whose constituent inferior and superior stimuli are shaped as paracentral scotomas.

A stimulus cycle lasts for a stimulus cycle time that is the sum of the stimulus pair presentation times.

3.11c Stimulus Set

The presentation to the eye of a patient of a selectable number (one or more) of stimulus cycles whose constituent stimulus pairs have the same shape comprises the presentation of a stimulus set. A stimulus set may, for example, be comprised of the presentation of 3 stimulus cycles, whose constituent stimulus pairs have inferior and superior stimuli that are shaped as paracentral scotomas.

A stimulus set lasts for a stimulus set time that is equal to the sum of its constituent stimulus cycle times.

3.11d Stimulus Test

The presentation to the eye of a patient of a selectable number (one or more) of stimulus sets comprises the presentation of a stimulus test. A stimulus test may, for example, be comprised of the presentation of 3 stimulus sets, such that: the first stimulus set presents 3 stimulus cycles whose constituent stimulus pairs have inferior and superior stimuli that are shaped as paracentral scotomas; and, the second stimulus set presents 3 stimulus cycles whose constituent stimulus pairs have inferior and superior stimuli that are shaped as Bjerrum's scotomas; and, the third stimulus set presents 3 stimulus cycles whose constituent stimulus pairs have inferior and superior stimuli that are shaped as peripheral scotomas.

Accordingly, the organization of the presentation of stimulus pairs by the invention may be represented symbolically as Stimulus Test=J Stimulus Sets of L Stimulus Cycles of K Stimulus Pairs $J \geq 1$; $L \geq 1$; $K \geq 1$.

In a preferred embodiment of the invention $J=K=L=3$

3.11e Stimulus Test in Greater Detail

As indicated supra., a stimulus test for a patient's eye comprises the presentation by the invention of a selectable number (one or more) of stimulus cycles. A stimulus test may be comprised of sets of stimulus cycles whose constituent stimulus pairs have mirror-image shapes that remain the same within any stimulus set, but may vary from one stimulus set to another. For example, a stimulus test may comprise the presentation by the invention of 3 stimulus sets, each of which presents 3 stimulus cycles such that:

[i] the first stimulus set comprises the presentation of 3 stimulus cycles, each of which comprises the presentation of 3 stimulus pairs having mirror-image shapes that correspond to a paracentral scotoma; and,

[ii] the second stimulus set comprises the presentation of 3 stimulus cycles, each of which comprises the presentation of 3 stimulus pairs having mirror-image shapes that correspond to a Bjerrum's scotoma; and,

[iii] the third stimulus set comprises the presentation of 3 stimulus cycles, each of which comprises the presentation of 3 stimulus pairs having mirror-image shapes that correspond to a peripheral scotoma.

3.12 Pupillary Response Curve

In the course of the presentation of stimuli to an eye, the invention computes a variety of clinical parameters from the variation of either the horizontal or vertical diameter of the pupil of an eye that is undergoing a test. For each presentation of a stimulus test, the invention computes a pupillary response curve that is a graph of pupillary diameters as a function of time in the course of the presentation of a stimulus test. In the case of any stimulus test comprising J stimulus sets of L stimulus cycles of K stimulus pairs, the invention records the diameter of the pupil as a function of time ("pupillary response curve") throughout the presentation of the test.

3.13 Cycle-Averaged Pupillary Response Curve for a Representative Stimulus Cycle For any given set comprising more than one stimulus cycle (L>1), the diameter of the pupil recorded in the course of each stimulus cycle is averaged with the diameter of the pupil recorded for every other stimulus cycle of the stimulus set, to obtain a cycle-averaged value of the pupillary diameter as a function of time over a representative stimulus cycle of the stimulus test ("cycle-averaged pupillary response curve"), which representative stimulus cycle is comprised of representative stimulus pairs. In effect, the pupillary diameters recorded for each stimulus cycle of the set are added to one another and then divided by the number of stimulus cycles in the stimulus set to obtain a cycle-averaged pupillary diameter as a function of time over a representative stimulus cycle of representative stimulus pairs ("cycle-averaged pupillary response curve").

For example, in a preferred embodiment of a test comprising 3 stimulus sets of 3 stimulus cycles of 3 stimulus pairs, the invention records the diameter of the pupil as a function of time throughout the presentation of the stimulus test. The invention may partition this recording over each of the 3 stimulus cycles comprising each stimulus set. For any given stimulus set of the stimulus test, the recorded variation of the diameter of the pupil in response to the 3 stimulus pairs presented in the first cycle of the stimulus set is added to the recorded variation of the diameter of the pupil in response to the 3 stimulus pairs presented in the second and third cycles of the stimulus set, and the resultant sum of pupillary diameters is divided by 3 and plotted against the cycle time to obtain a cycle-averaged variation in the diameter of the pupil as a function of time over a representative stimulus cycle of the stimulus set, ("cycle-averaged pupillary response curve), which representative stimulus cycle is comprised of 3 representative stimulus pairs. This is shown in FIG. 8

Figure 8:
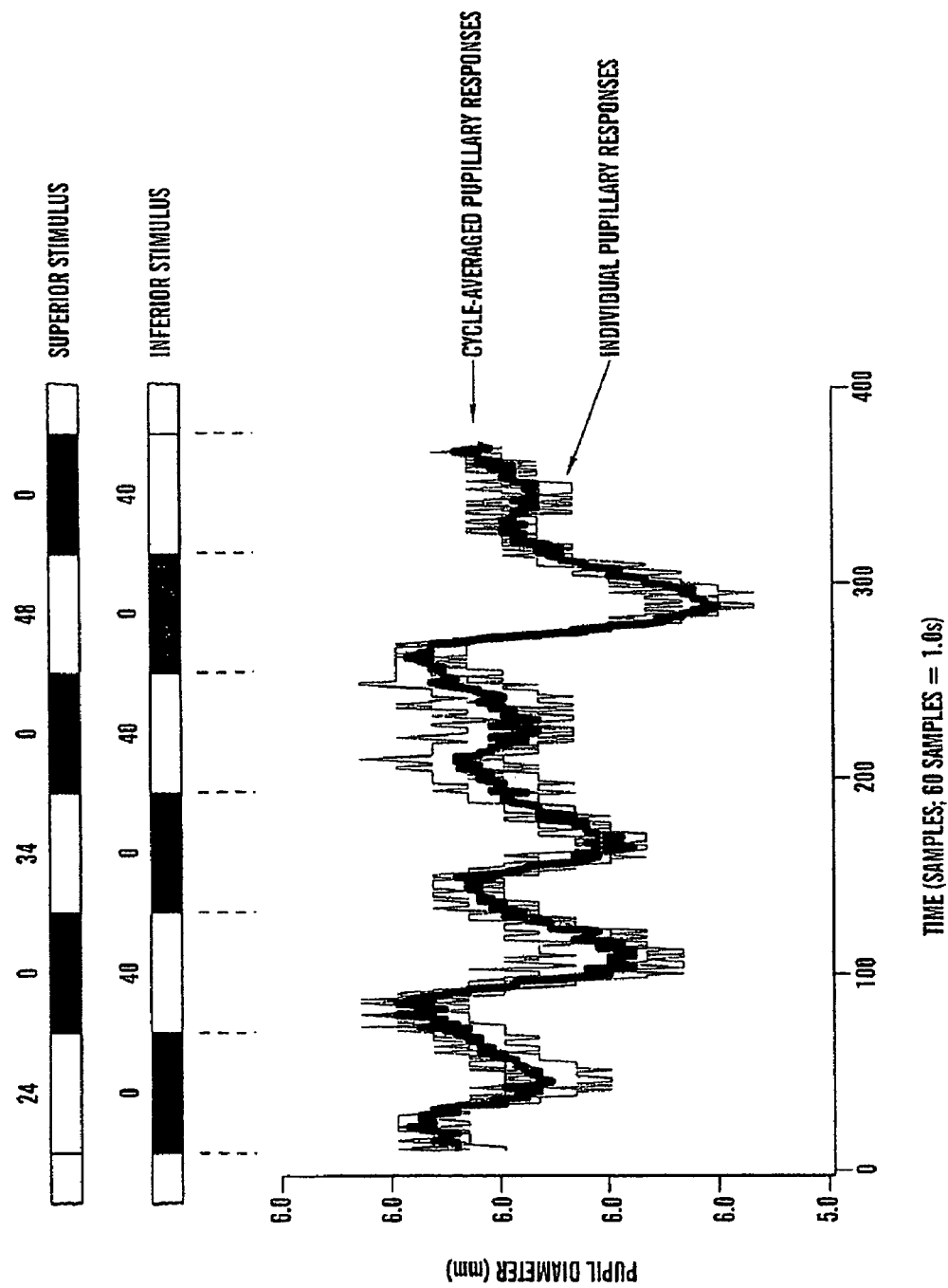
FIG. 8 shows a schematic representation of the presentation of a stimulus cycle comprising 3 stimulus pairs as a function of time above a graph of the diameter of the pupil of an eye of a patient, to which the stimulus pair is being presented, as a function of time.

FIG. 8 shows a schematic representation of the presentation of a stimulus cycle comprising 3 stimulus pairs as a function of time ("time course of a stimulus pair") above a graph of the diameter of the pupil of an eye of a patient, to which the stimulus pair is being presented, as a function of time.

The time course of a stimulus pair is schematically shown by two horizontal parallel bars. The upper bar, labeled represents the on/off status of an exemplary shaped superior stimulus of a stimulus pair presented to a patient's eye; and, the lower bar represents the on/off status of an exemplary shaped inferior stimulus of a stimulus pair presented to a patient's eye. The bars are accordingly labeled "superior stimulus" and "inferior stimulus." The time of the onset of presentation of each stimulus is identified by the label "stimulus onset." Each bar is divided into segments, having an exemplary luminance of the stimulus, measured in cd/m, which is indicated numerically above each segment. The length of each segment in each horizontal bar is proportional to the duration of the stimulus in sixtieths of a second, and corresponds to an abscissa, appearing below, that is scaled in sixtieths of a second.

In FIG. 8, the superior stimulus bar indicates an exemplary superior stimulus presentation to the eye of a patient that is: on at an approximate exemplary luminance of 24 cd/m² for about 1 second, then off at an approximate exemplary luminance of 0 cd/m$^2$ for about 1 second; then, on again at an approximate exemplary luminance of 34 cd/m$^2$ for about 1 second, then off again at an approximate exemplary luminance of 0 cd/m$^2$ for about 1 second; and, finally on yet again at an approximate exemplary luminance of 48 cd/m$^2$ for about 1 second, then off yet again at an approximate exemplary luminance of 0 cd/m$^2$ for about 1 second.

In FIG. 8, the inferior stimulus bar indicates that when the exemplary superior shaped stimulus courses through its on/off sequence as described, the exemplary shaped inferior stimulus courses through a simultaneous and corresponding sequence of on/off cycles between an approximate exemplary fixed luminance of 40 cd/m$^2$ for about 1 second and an approximate exemplary luminance of 0 cd/m$^2$ for about 1 second.

Appearing beneath the time course of a stimulus pair in FIG. 8 is the time course of corresponding pupillary response curves. The thin lines, labeled "individual pupillary responses," represent the superposition of pupillary response curves arising in the course of 3 presentations of the stimulus cycle shown schematically by the horizontal bars above. The thick line, labeled "cycle-averaged pupillary response," represents the cycle-averaged pupillary response obtained by averaging the individual pupillary responses. The graph displays the cycle-averaged pupillary response as a function of time over a stimulus cycle that is a representative of any of the three stimulus cycles from which the individual pupillary response curves were obtained. Accordingly, the representative stimulus cycle contains 3 representative stimulus pairs.

The cycle-averaged pupillary response curve shows a graph of the average variation of the diameter of the pupil, in millimeters, in response to the presentation of a stimulus pair as a function of time, in units of sixtieths of a seconds, e.g., 60 units on the abscissa represents 1 sec; 120 units on the abscissa represents 2 sec, etc.

3.14 Computed Parameters

Figure 15A:
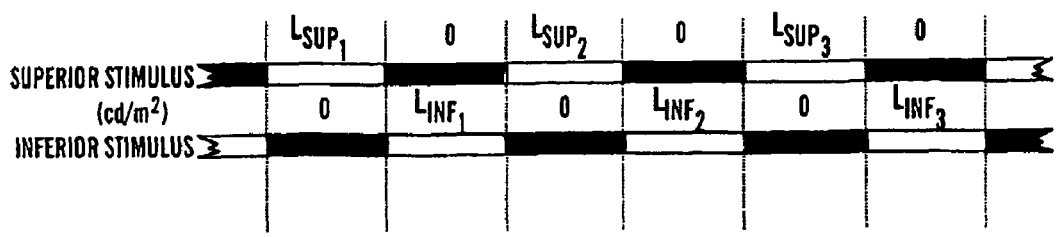
FIG. 15a shows a schematic representation of an exemplary Type II stimulus pair.

For each stimulus pair of a representative stimulus cycle, the invention uses the cycle-averaged pupillary response curve to compute:

[i] a cycle-averaged superior pupillary response amplitude Ra(sup) and a corresponding shaped superior stimulus luminance L(sup) that has evoked the cycle-averaged superior pupillary response amplitude (further described in conjunction with FIG. 15a, infra.);

[ii] a cycle-averaged inferior pupillary response amplitude Ra(inf) and a corresponding shaped inferior stimulus luminance L(inf) that has evoked the cycle-averaged inferior pupillary response amplitude (further described in conjunction with FIG. 15a, infra.);

[iii] a cycle-averaged pupillary response balance $$RB=[Ra(sup)-Ra(inf)]/[Ra(sup)+Ra(inf)] \quad (1.0)$$

(further described in conjunction with FIG. 15a, infra.); and,

[iv] a corresponding luminance ratio comprising the ratio of the luminance of the shaped inferior stimulus of a stimulus pair to the luminance of the shaped superior stimulus of the stimulus pair $$LR=L(inf)/L(sup); \text{ or,} \quad (2.0)$$

the ratio of the luminance of the shaped superior stimulus of a stimulus pair to the luminance of the shaped inferior stimulus of the stimulus pair $$LR=L(sup)/L(inf); \quad (3.0)$$

Figure 15B:
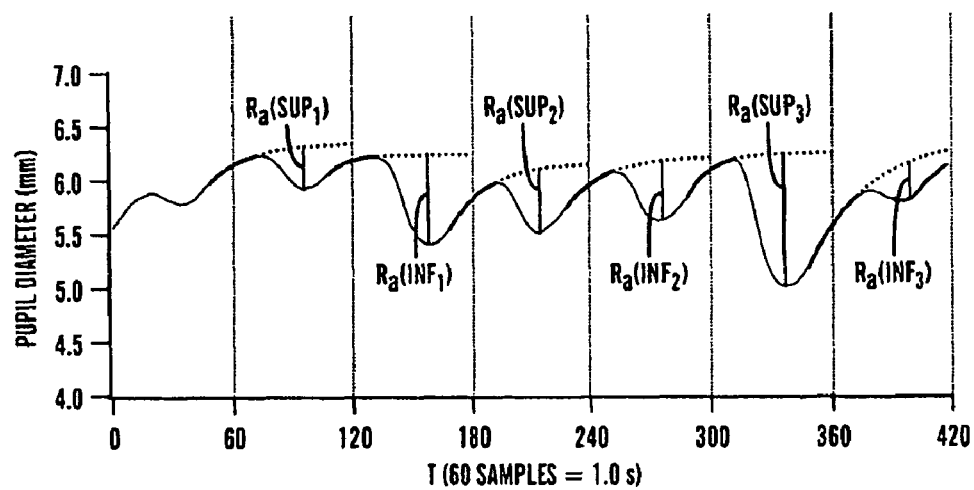
FIG. 15b shows a graph of the horizontal diameter of the pupil of an eye of a patient to which the Type II stimulus pair is being presented as a function of time.
Figure 15C:
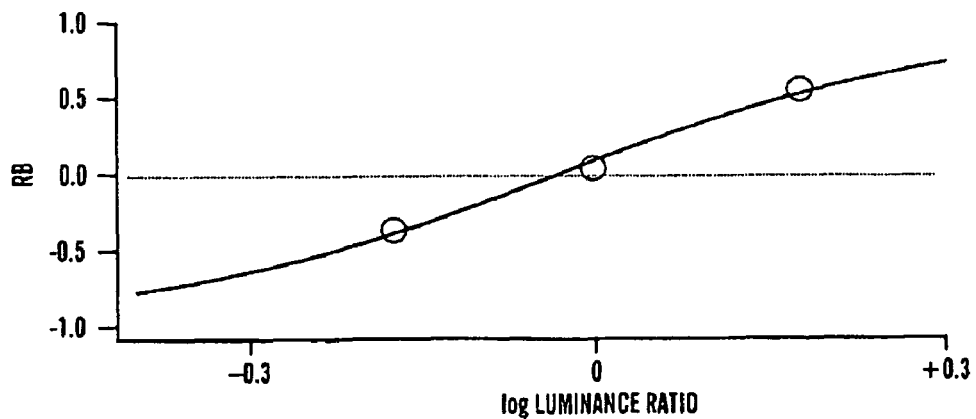
FIG. 15c is an exemplary graph of a patient's response balances fitted to a sigmoid function of luminance ratios LR, where the abscissa is scaled in units of the logarithm of the luminance ratios.

(further described in conjunction with FIG. 15c, infra.).

3.15 Stimulus Pair Response Curve

For each representative stimulus cycle, the invention computes a stimulus pair response curve by fitting the values of the cycle-averaged pupillary response balances computed for each stimulus pair of the representative stimulus cycle to a sigmoid function of the luminance ratio of each stimulus pair of the representative stimulus cycle (further described in conjunction with FIG. 15c, infra.).

3.16 Balanced Luminance Ratio

For each presentation of a stimulus test, the invention computes a balanced luminance ratio at which the cycle-averaged pupillary response balance is equal to about zero.

A value of the balanced luminance ratio that is substantially less than zero is indicative of an abnormality of the visual sensitivity of the superior retina and a value of the balanced luminance ratio that is greater than zero is indicative of an abnormality of the visual sensitivity of said inferior retina. (further described in conjunction with FIGS. 16a through 16c, infra.).

3.17 Structure of the Invention

As used herein, the word "computing device" means, inter alia, a microprocessor, server, desktop computer, laptop computer, personal digital assistant or other form of hand-held or portable computer.

As used herein, the term "data entry device" means, inter alia, a keyboard, keypad, stylus-based data entry device or a touch-based data entry device, such as a touchpad.

As used herein, the term "display device" means, inter alia, a computer monitor, liquid crystal display panel, television set or printer or other output device.

As used herein, the term "luminance" of a stimulus means the intensity of a stimulus; and, inasmuch as the luminance of a stimulus is presented by the invention against a selectably fixed background luminance, the term "luminance" of a stimulus also means the contrast of the stimulus.

As used herein, the term "compute" means to effect a computation, calculation, recordation, measurement, plot or graph.

Figure 9:
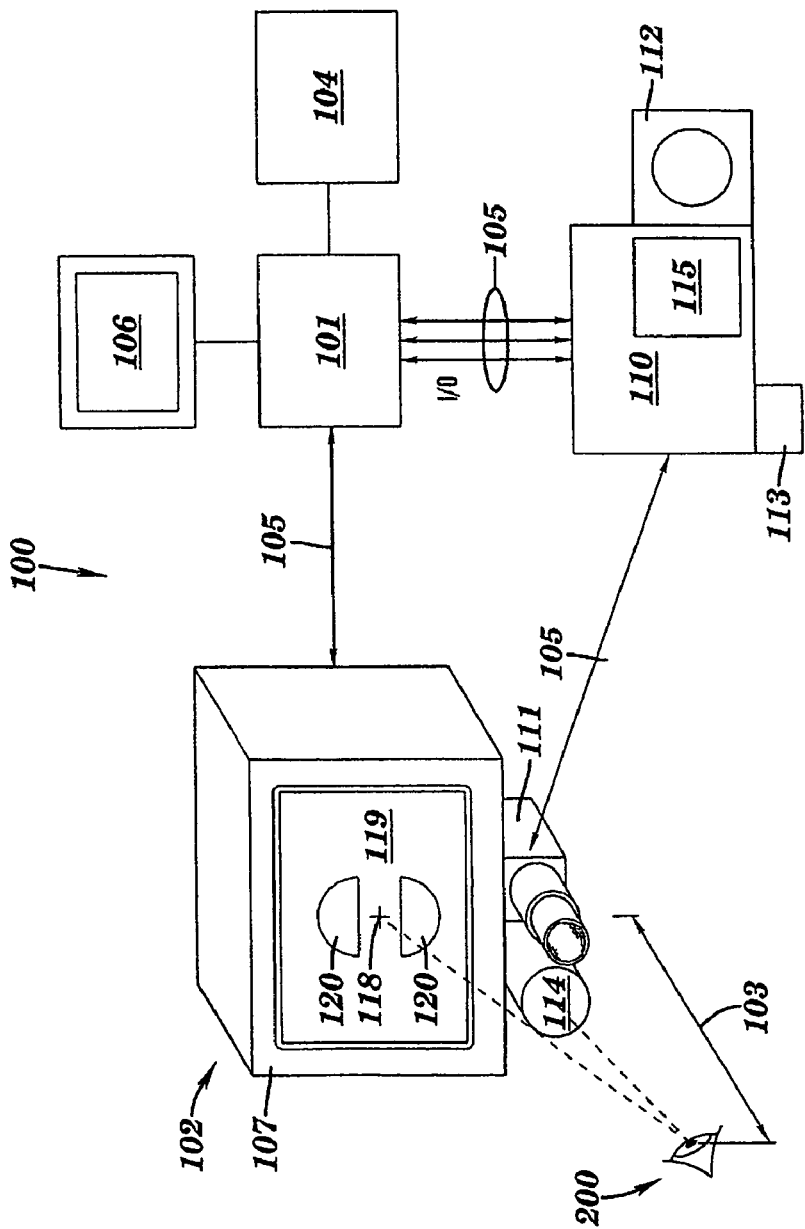
FIG. 9 is a schematic illustration of the invention.

FIG. 9 is a schematic illustration of the invention.

As shown in FIG. 9, invention 100 is comprised of computing device 101 operationally connected by digital input/output ("I/O") lines 105 to data entry device 104, operator display device 106, stimulus pair display device 102 and pupillometer 110.

Computing device 101 may, for example, comprise a personal computer, such as, for example, a Macintosh G3 computer. Computing device 101 runs operational software, such as, for example, Matlab5.2 (The Math Works).

Stimulus pair display device 102 may, for example, comprise a personal computer monitor, such as, for example, a 21-inch Radius Press View 21SR, having an active area of 38.0 cm×27.8 cm, a resolution of 832×624 pixels, and frame rate of 75 Hz. Stimulus pair display device 102 may, for example, be operationally controlled by, and interface with, computing device 101, using a Psychophysics Toolbox with a Wang Interface in Matlab, providing high-level access to a C-language VideoToolbox.

The invention's operational software may be programmed to generate a stimulus pair 120 centered upon a movable fixation icon 118 appearing on display screen 107 of stimulus pair display device 102. Display screen background 119, against which stimulus pair 120 is displayed, has a selectable background luminance that may, for example, be set at a value of about 5.5 cd/m².

The invention's operational software is programmed to generate a stimulus pair for presentation upon display screen 107 of stimulus pair display device 102 against a selectable coordinate system (not shown in FIG. 9), within which movable fixation icon 118 is disposed, such as. Movable fixation icon 118 may, for example, have the form of a cross, circle or other suitable shape, that identifies a fixation point for an eye being tested by the invention. The coordinate system against which the stimulus pair is presented may, for example, be a polar coordinate system centered on the fixation point or a Cartesian coordinate system centered upon the fixation point or a coordinate systems consistent with the use of automated visual field perimeters.

The invention's operational software is also be programmed to generate for presentation on operator display device 106 an interactive menu comprising operational means for selecting, inter alia:

- coordinates of the fixation point within the selectable coordinate system;
- a shape of the shaped superior stimulus and the shaped inferior stimulus of a stimulus pair;
- an area of the shaped superior stimulus and the shaped inferior stimulus of a stimulus pair;
- a luminance of the shaped superior stimulus of a stimulus pair
- a luminance of the shaped inferior stimulus of a stimulus pair
- a luminance of the selectable background luminance
- a shaped superior stimulus presentation time for the shaped superior stimulus of a stimulus pair;
- a shaped inferior stimulus presentation time for the shaped superior stimulus of a stimulus pair;
- a number of stimulus pairs comprising a stimulus cycle
- a stimulus cycle time
- a number of stimulus cycles comprising a stimulus set
- a stimulus set time
- a number of stimulus sets comprising a stimulus test
- a stimulus test time
- an on/off status for pupillometer 110.

Computing device 101 also runs data analysis software, such as, for example, data analysis software written with IgorPro 4.0 (WaveMetrics, Inc.) to record, measure, compute and analyze a patient's responses to a stimulus test. Included among these data are:

- timing signals for the activating stimulus presentations
- timing signals for terminating stimulus presentations
- the patient's horizontal or vertical pupillary diameter at specified times
- a superior pupillary response amplitude (described infra.)
- a corresponding luminance of a shaped superior stimulus
- an inferior pupillary response amplitude (described infra.)
- a corresponding luminance of a shaped inferior stimulus
- Included among these computations are:
- pupillary response balances (described infra.)
- luminance ratios (described infra.)
- pupillary response curves (described infra.)
- stimulus pair response curves (described infra.)
- balanced luminance ratios (described infra.)

Pupillometer 110 comprises pupillometer video camera 111, eye display device 112, pupillometer computing device 113, pupillometer light source 114, and pupillometer display device 115.

Pupillometer 110 may, for example, be a computerized pupillometer, such as, for example, a model EC-101 PC-based dark pupil pupillometer system manufactured by ISCAN, and wherein pupillometer light source 114 comprises an infrared spotlight, pupillometer computing device 113 comprises a PC, and pupillometer display device 115 comprises a PC monitor.

Pupillometer light source 114 and pupillometer video camera 111 are disposed at about the same distance from eye 200 as stimulus pair display device 102, and appropriately aligned so that the pupil of eye 200 is visualized on pupillometer display device 115. The pupil of eye 200 is also displayed by eye display device 112.

Pupillometer video camera 111 is further disposed below stimulus pair display device 102 such that the geometric center of the lens (not shown in FIG. 9) of pupillometer video camera 111 is vertically aligned with the geometric center of the display screen (not shown in FIG. 9) of stimulus pair display device 102.

Stimulus pair display device 102 may be disposed at a distance from the anterior surface of an eye 200 as indicated by dashed line 103 in FIG. 9. Distance 103 may, for example, be about 75 cm, so that display 107 subtends a visual angle at the eye of about 29.1° horizontally and about 21.8° vertically, when eye 200 is vertically positioned midway between the vertical midpoint of stimulus pair display device 102 and the vertical midpoint of pupillary video camera 111.

Pupillometer 110 may be programmed to record the vertical or horizontal diameter of a pupil of eye 200 at a selectable recording frequency, such as, for example 60 times/second. Pupillometric data, such as, for example, pupillary amplitudes of constriction, are saved in recordable media (not shown in FIG. 9) in files, such as, for example, software-specific raw data files and ASCII files.

3.18 Stimulus Pair Design

Different parts of the retina are associated with different visual sensitivities for stimulating a PLR. The macula in the central retina has the greatest sensitivity for stimulating a PLR. The visual sensitivity of the retina for stimulating a PLR decreases rapidly as the stimulus moves radially away from the macula.

In order to stimulate a PLR from which an index of the state of visual function in glaucoma may be computed, the shaped superior light stimulus of a stimulus pair and the shaped inferior light stimulus of a stimulus pair are designed to respectively encompass a superior and inferior region of retina with sufficient visual sensitivity for stimulating a PLR and to respectively encompass a superior and inferior region of the retina most likely to demonstrate a decline in visual function if it the area of the visual field has been damaged by glaucoma.

Figure 11:
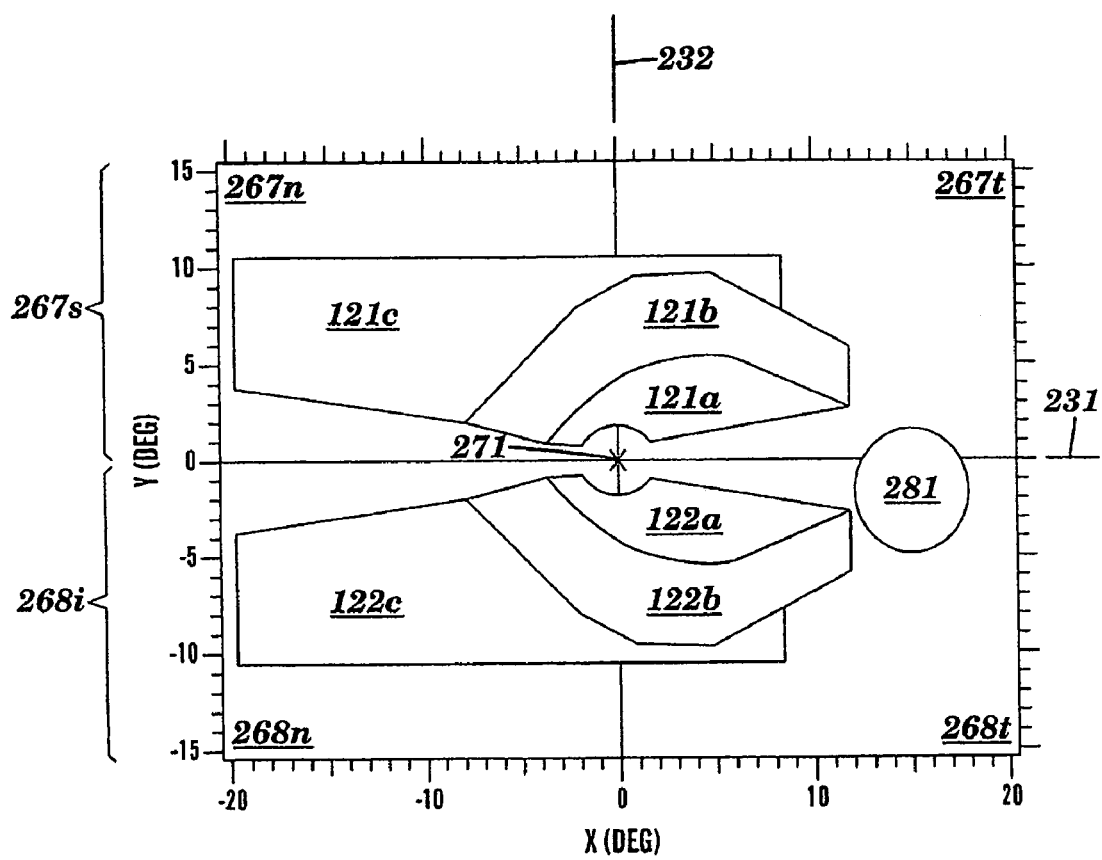
FIG. 11 is a schematic illustration of the superposition of three exemplary stimulus pairs as displayed to a right retina.

The a visual field covered by the set of stimuli used in the present invention corresponds to a retinal area that is bounded by about 30° horizontally and by about 20° vertically ("central retinal area"). Horizontally, the retinal area extends from about 20° nasal to the fixation point to about 10° degrees temporal to the fixation point; and vertically, from about 10° superior to the fixation point to about 10° inferior to the fixation point. (FIG. 11, infra.)

Within the central retinal area, the stimulus pairs presented by the invention encompass retinal regions having adequate visual sensitivity for stimulating a PLR. Additionally, by presenting mirror-image stimuli to the superior and inferior retina that are shaped to emulate known patterns of glaucomatous retinal loss, the correlation between stimulus shape and probable glaucomatous damage is maximized.

As indicated, supra., the invention administers an objective clinical test to a patient that compares the visual sensitivity of the superior retina to the visual sensitivity of the inferior retina ("horizontally paired retinal areas") of the same eye, by alternately presenting a shaped superior light stimulus to the superior retina and a shaped inferior light stimulus to the inferior retina, which shaped superior and inferior light stimuli are mirror images of one another with respect to horizontal meridian 231 (FIG. 2, FIG. 4, FIG. 5), and have shapes corresponding to visual field defects that are characteristic of glaucoma. The symmetrically paired superior and inferior light stimuli are used to stimulate corresponding pairs of pupillary light responses whose amplitudes of constriction are measured, and from which a cycle-averaged pupillary response balance (described infra.) is computed as a function of the luminance of the stimuli, in the form of a parameter called a luminance ratio (described infra.).

Figure 10A:
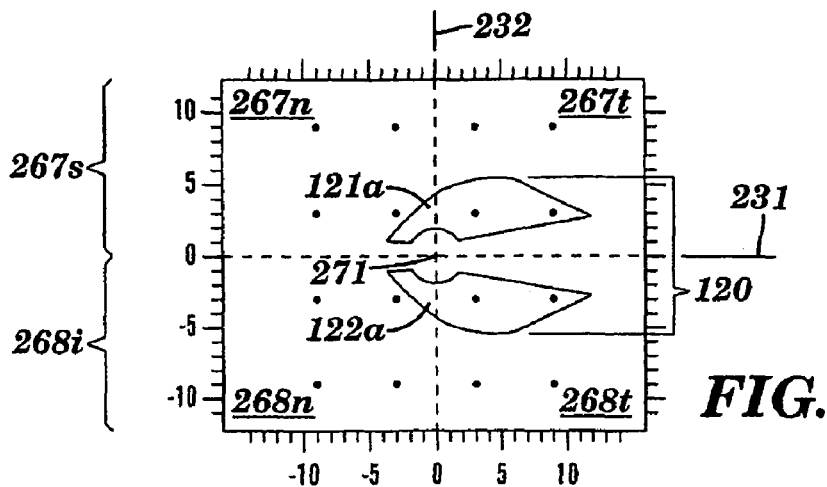
FIG. 10a is a schematic illustration of a first exemplary stimulus pair for display to a right retina in the form of paired superior and inferior light stimuli, shaped as mirror-image paracentral scotomas that are symmetric about a horizontal meridian.
Figure 10B:
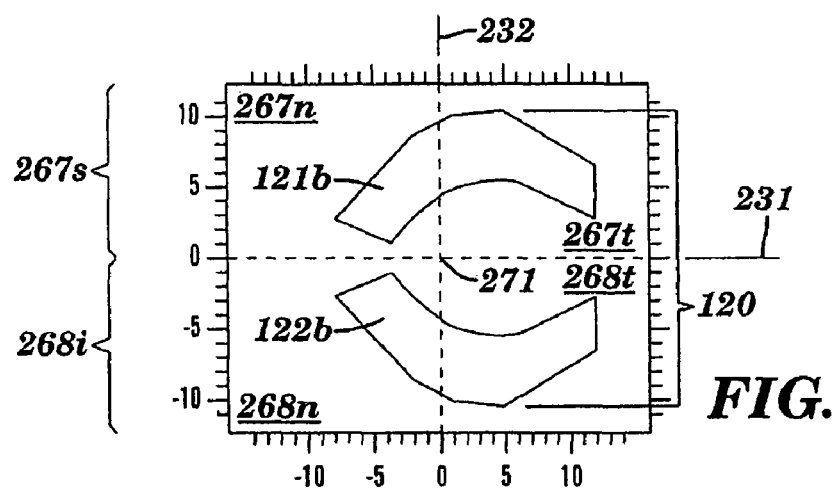
FIG. 10b is a schematic illustration of a second exemplary stimulus pair for display to a right retina in the form of paired superior and inferior light stimuli, shaped as mirror-image Bjerrum's scotomas that are symmetric about a horizontal meridian.
Figure 10C:
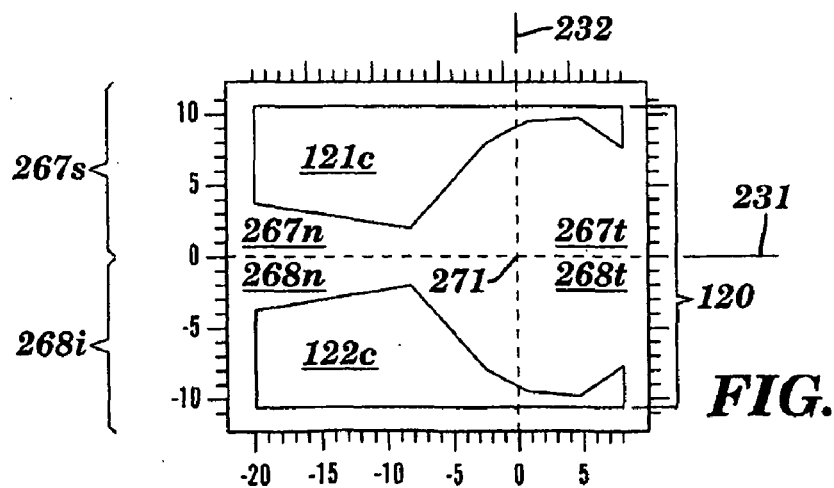
FIG. 10c is a schematic illustration of a third exemplary stimulus pair for display to a right retina in the form of paired superior and inferior light stimuli, shaped as mirror-image peripheral scotomas that are symmetric about a horizontal meridian.

Exemplary stimulus pairs for presentation to a patient are shown in FIGS. 10a through 10c.

FIG. 10a is a schematic illustration of a first exemplary stimulus pair 120 for display to a right retina in the form of paired superior 121a and inferior 122a light stimuli, shaped as mirror-image paracentral scotomas that are symmetric about the horizontal meridian.

FIG. 10b is a schematic illustration of a second exemplary stimulus pair 120 for display to a right retina in the form of paired superior 121b and inferior 122b light stimuli, shaped as mirror-image Bjerrum's scotomas that are symmetric about the horizontal meridian.

FIG. 10c is a schematic illustration of a third exemplary stimulus pair 120 for display to a right retina in the form of paired superior 121c and inferior 122c light stimuli, shaped as mirror-image peripheral scotomas that are symmetric about the horizontal meridian.

In FIGS. 10a through 10c, each stimulus pair 120 comprises a shaped superior light stimulus 121a or 121 b or 121c located in the superior visual field 267S and a shaped inferior light stimulus 122a or 122 b or 122c located in the inferior visual field 268I, bordered by a uniform display screen background (not shown in FIGS. 10a through 10c) having a luminance level, such as, for example, 5 cd/m$^2$, that is lower than the luminance level of either the shaped superior light stimulus 121a or 121 b or 121c or the shaped inferior light stimulus 122a or 122 b or 122c. In FIGS. 10a through 10c, superior shaped light stimulus 121a or 121 b or 121c and inferior shaped light stimulus 122a or 122 b or 122c are mirror images of each other with respect to horizontal meridian 231. In FIGS. 10a through 10c, a fixation point toward which a patient is directed to direct the gaze of the eye being tested is represented by a fixation cross 271.

In FIGS. 10a through 10c, the vertical scale indicates vertical proximity to the fixation point 271 in degrees, with negative values corresponding to the visual field inferior to horizontal meridian 231. The horizontal scale indicates horizontal proximity to the fixation point 271 in degrees, with negative values corresponding to the field to the left of vertical meridian 232.

As shown in FIGS. 10a through 10c, each superior and inferior light stimulus is shaped to cover a retinal region within a retinal area about 20° horizontally by 10° vertically ("central retinal area"). For the peripheral stimulus shown in FIG. 10c, fixation point 271 is decentered laterally, so that the retinal region covered by the peripheral stimulus extends to 20° horizontally. The shapes of both the superior and inferior light stimuli comprising a stimulus pair are designed to maximize the correlation between an area of the retina selected for light stimulation and the probability of glaucomatous damage arising in that area.

Each exemplary stimulus pair—paracentral, Bjerrum's and peripheral—comprises a different area of highly-likely glaucomatous loss in the central retinal area and its corresponding visual field. When superimposed upon one another, the three exemplary stimulus pairs cover the area of the central retina and its corresponding visual field that is most vulnerable to glaucomatous loss. This is illustrated in FIG. 11 and FIG. 12.

FIG. 11 is a schematic illustration of the superposition of three exemplary stimulus pairs as displayed to a right retina. In FIG. 11, the vertical scale indicates vertical proximity to the fixation point 271 in degrees, with negative values corresponding to the visual field inferior to horizontal meridian 231. The horizontal scale indicates horizontal proximity to the fixation point 271 in degrees, with negative values corresponding to the field to the left of vertical meridian 232.

Figure 12:
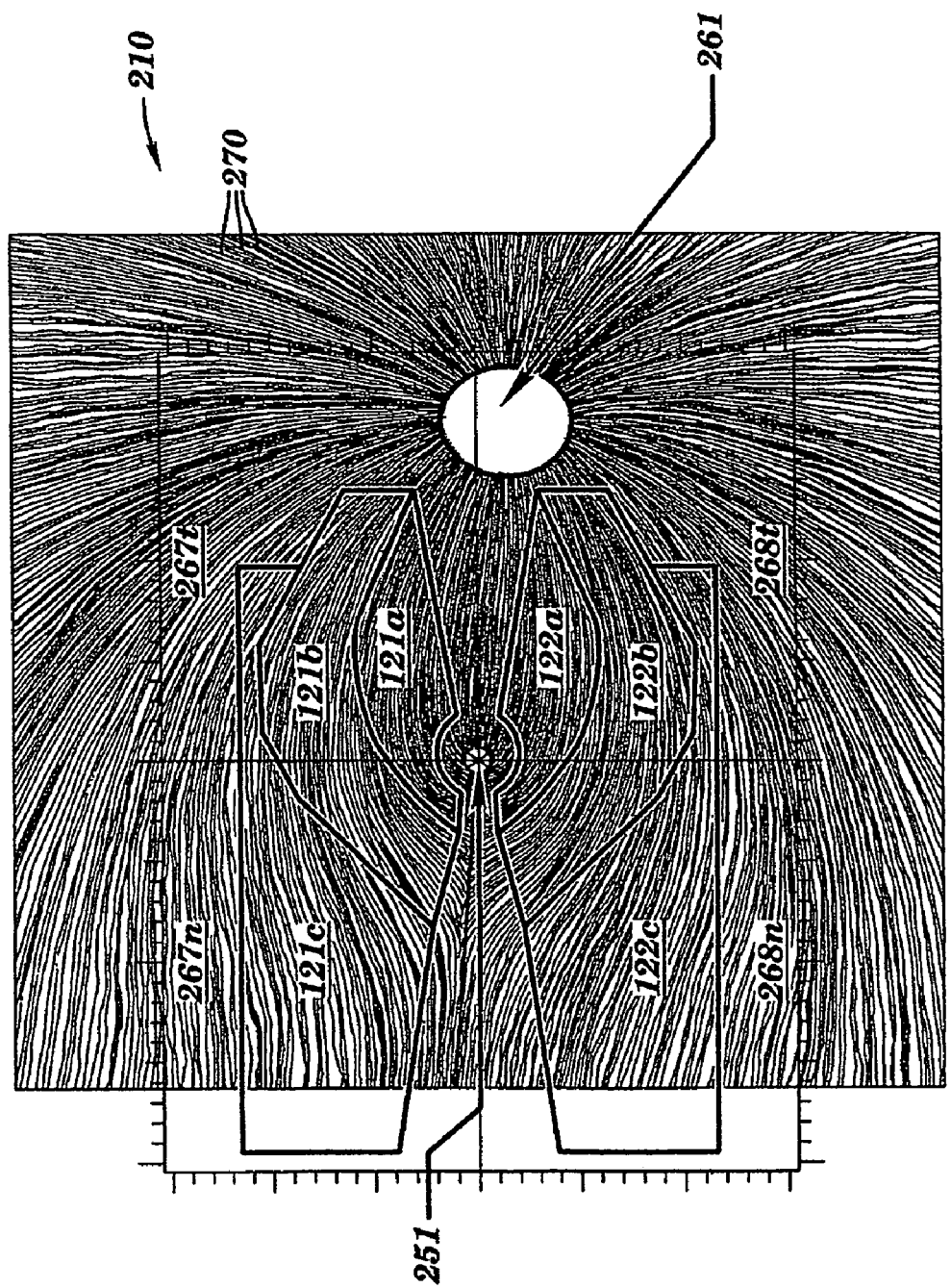
FIG. 12 is a schematic illustration of the superposition of three exemplary stimulus pairs as viewed by a right retina.

FIG. 12 is a schematic illustration of the superposition of three exemplary stimulus pairs when viewed by a right retina.

3.19 Stimulus Pair Presentation by the Invention

In an exemplary single presentation of a stimulus pair 120 (FIGS. 10a through 10c), the paired superior 121a or 121b or 121c (FIGS. 10a through 10c) and inferior 122a or 122b or 122c (FIGS. 10a through 10c) shaped stimuli of which it is comprised are alternately turned on and off in the respective superior 267S and inferior 268I visual fields, as follows: first, the shaped superior stimulus 121a or 121 b or 121c (FIGS. 10a through 10c) is presented by the invention (i.e., turned "on") for a superior stimulus presentation time, such as, for example, one second, and the shaped inferior stimulus 122a or 122b or 122c (FIGS. 10a through 10c) is substantially dimmed or not presented by the invention (i.e., turned "off"); then, the shaped inferior stimulus 122a or 122b or 122c (FIGS. 10a through 10c) is turned on for an inferior stimulus presentation time, such as, for example, one second, and the shaped superior stimulus 121a or 121b or 121c (FIGS. 10a through 10c) is turned off. Whenever either shaped stimulus is turned on, the patient's pupil constricts.

3.20 Exemplary Type I Stimulus Pair

Presentation of superior and inferior light stimuli within a stimulus cycle may be conducted using a variety of selectable presentation patterns.

Figure 13B:
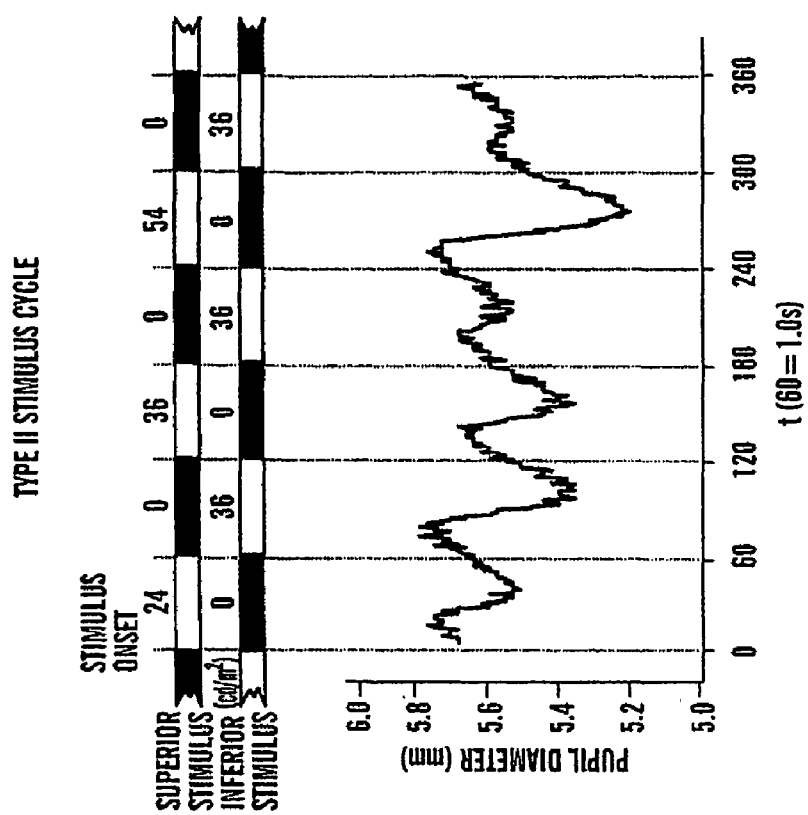
FIG. 13b shows a schematic representation of the pattern of presentation of an exemplary Type II stimulus cycle as a function of time across a representative stimulus cycle above a graph of the horizontal diameter of the pupil of an eye, to which the Type II stimulus cycle is being presented, as a function of time.
Figure 13A:
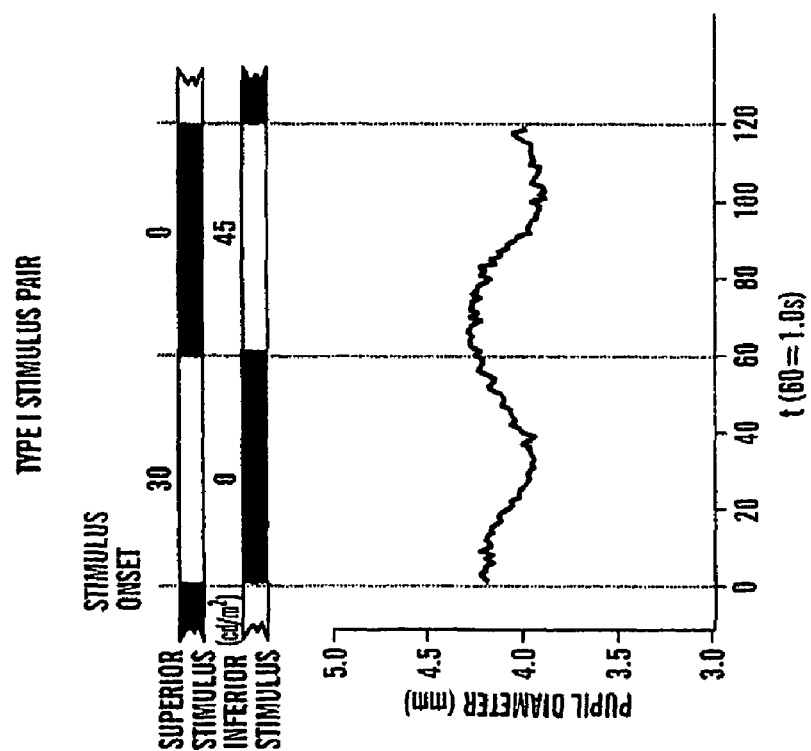
FIG. 13a shows a schematic representation of the pattern of presentation of an exemplary Type I stimulus pair as a function of time across a representative stimulus cycle above a graph of the horizontal diameter of the pupil of an eye, to which the Type I stimulus pair is being presented, as a function of time.

FIG. 13a shows a schematic representation of the presentation pattern of an exemplary Type I stimulus pair as a function of time ("time course of a stimulus pair") across a representative stimulus cycle above a graph of the horizontal diameter of the pupil of an eye of a patient, to which the exemplary Type I stimulus pair is being presented, as a function of time (cycle-averaged pupillary response curve).

The time course of the Type I stimulus pair is schematically shown by two horizontal parallel bars. The upper bar represents the on/off status of an exemplary shaped superior stimulus of a stimulus pair presented to a patient's eye; and, the lower bar represents the on/off status of an exemplary shaped inferior stimulus of a stimulus pair presented to a patient's eye. The bars are accordingly labeled "superior stimulus" and "inferior stimulus." The time of the onset of presentation of each stimulus is identified by the label "stimulus onset." Each bar is divided into segments having an exemplary luminance of the stimulus measured in cd/m$^2$, which is indicated numerically above each segment. The length of each segment in each horizontal bar is proportional to the duration of the stimulus in sixtieths of a second, and corresponds to an abscissa, appearing below, that is scaled in sixtieths of a second.

In FIG. 13a, the superior stimulus bar indicates a presentation of an exemplary shaped superior stimulus to the eye of a patient that is on at an approximate exemplary luminance of 30 cd/m for about 1 second, and then off at an approximate exemplary luminance of 0 cd/m² for about 1 second. In FIG. 13a, the inferior stimulus bar indicates that when the exemplary shaped superior stimulus is on at an approximate exemplary luminance of 30 cd/m² for about 1 second, the exemplary shaped inferior stimulus is off at an approximate exemplary luminance of 0 cd/m for about one second; and, when the exemplary shaped superior stimulus is off at an approximate exemplary luminance of 0 cd/m² for about 1 second, the exemplary shaped inferior stimulus is on at an approximate exemplary luminance of 45 cd/m² for about one second.

Appearing beneath the time course of a stimulus pair in FIG. 13a is the corresponding cycle-averaged pupillary response curve. The cycle-averaged pupillary response curve shows a graph of the average variation of the horizontal diameter of the pupil, in millimeters, in response to the presentation of the Type I stimulus pair as a function of time, in units of sixtieths of a seconds, e.g., 20 units on the abscissa represents ⅓ sec; 40 units on the abscissa represents ⅔ sec, etc.

Referring to FIG. 13a, it can be seen that for the exemplary Type I stimulus pair, each exemplary shaped light stimulus of the stimulus pair may be presented at a different fixed luminance level, such as, for example, about 45 cd/m² for the inferior shaped light stimulus, whenever it is on, and about 30 cd/m² for the superior shaped light stimulus, whenever it is on.

Accordingly, a Type I stimulus pair presentation is an example of the presentation of a steady-state-luminance stimulus pair, a selectable number (one or more) of which may comprise a steady-state-luminance stimulus cycle, that may last for a steady-state-luminance stimulus cycle time, such as, for example, about 6 seconds.

A selectable number (one or more) of steady-state-luminance stimulus cycles may be presented by the invention to comprise a steady-state luminance stimulus set; and a selectable number (one or more) of steady-state luminance stimulus sets may comprise a steady-state luminance stimulus test for an eye. A steady-state-luminance stimulus test lasts for steady-state-luminance stimulus test time that is equal to the sum of the steady-state-luminance stimulus cycle times (plus the duration of any intervening times between stead-state-luminance stimulus cycle times).

For example, a Type I stimulus pair whose superior and inferior stimuli have a first shape may be presented 3 times to form a first steady state stimulus cycle. The first steady state stimulus cycle may be presented 2 more times to form a first steady state stimulus set. The steady state stimulus set may be presented again as a second stimulus set whose constituent stimulus pairs have a second shape. The steady state stimulus set maybe presented yet again as a third stimulus set whose constituent stimulus pairs have a third shape. The presentation of the three steady state stimulus sets may comprise the presentation the Type I steady-state-luminance stimulus test.

Alternatively stated, an exemplary Type I steady-state luminance stimulus test may be comprised of 3 steady-state stimulus sets, each presenting 3 steady-state stimulus cycles as follows:

[i] a first steady-state luminance stimulus cycle lasting about 6 seconds is presented to an eye, and the presentation is repeated 2 more times, for a total of three presentations of, for example, a pre-selected symmetrically paired superior and inferior stimulus having the shape of a paracentral scotoma thereby forming a first steady-state luminance stimulus set that lasts for 3×6=18 seconds; then,

[ii] a second steady-state luminance stimulus cycle lasting about 6 seconds is presented to the same eye, and is repeated 2 more times, for a total of three presentations of, for example, a pre-selected symmetrically paired superior and inferior stimulus having the shape of a Bjerrum's scotoma thereby forming a second steady-state luminance stimulus set that lasts for 3×6=18 seconds; then,

[iii] a third steady-state luminance stimulus cycle lasting about 6 seconds is presented to the same eye, and is repeated 2 more times, for a total of three presentations of, for example, a pre-selected symmetrically paired superior and inferior stimulus having the shape of a peripheral scotoma thereby forming a third steady-state luminance stimulus set that lasts for 3×6=18 seconds.

Thereafter, the same three sets of three repetitions of a steady-state stimulus cycle may be presented to the other eye for each of the three exemplary pre-selected symmetrically paired superior and inferior stimulus shapes; however, the sequence of presentation of the three exemplary pre-selected symmetrically paired superior and inferior stimulus shapes may differ from that used for the first eye.

Applying the foregoing timing for each of the three sets of steady-state stimulus cycles presented to an eye in a stimulus test, and allowing a rest time of 30 seconds following the presentation of the first set of three exemplary steady-state stimulus cycles and following the presentation of the second set of three exemplary steady-state stimulus cycles, the total time for administering a Type I steady-state luminance stimulus test is $$18[3\times6] \text{ sec} + 30 \text{ sec} + 18[3\times6] \text{ sec} + 30 \text{ sec} + 18[3\times6] \text{ sec} = 114 \text{ sec}$$

3.21 Exemplary Type II Stimulus Pair and Type II Stimulus Cycle

FIG. 13b shows a schematic representation of the pattern of presentation of an exemplary Type II stimulus cycle as a function of time across a representative stimulus cycle ("time course of a stimulus pair") above a graph of the horizontal diameter of the pupil of an eye of a patient, to which the stimulus pair is being presented, as a function of time (cycle-averaged pupillary response curve).

The time course of a stimulus pair is schematically shown by two horizontal parallel bars. The upper bar represents the on/off status of an exemplary shaped superior stimulus of a stimulus pair presented to a patient's eye; and, the lower bar represents the on/off status of an exemplary shaped inferior stimulus of a stimulus pair presented to a patient's eye. The bars are accordingly labeled "superior stimulus" and "inferior stimulus." The time of the onset of presentation of each stimulus is identified by the label "stimulus onset." Each bar is divided into segments, having an exemplary luminance of the stimulus, measured in cd/m², which is indicated numerically above each segment. The length of each segment in each horizontal bar is proportional to the duration of the stimulus in sixtieths of a second, and corresponds to an abscissa, appearing below, that is scaled in sixtieths of a second.

In FIG. 13b, the superior stimulus bar indicates an exemplary superior stimulus presentation to the eye of a patient that is: on at an approximate exemplary luminance of 24 cd/m² for about 1 second, then off at an approximate exemplary luminance of 0 cd/m² for about 1 second; then, on again at an approximate exemplary luminance of 36 cd/m² for about 1 second, then off again at an approximate exemplary luminance of 0 cd/m² for about 1 second; and, finally on yet again at an approximate exemplary luminance of 54 cd/m² for about 1 second, then off yet again at an approximate exemplary luminance of 0 cd/m² for about 1 second, all against an exemplary fixed background luminance of 5.5 cd/m².

In FIG. 13b, the inferior stimulus bar indicates that when the exemplary superior shaped stimulus courses through its on/off sequence as described, the exemplary shaped inferior stimulus courses through a simultaneous and corresponding sequence of on/off cycles between an approximate exemplary fixed luminance of 36 cd/m² for about 1 second and an approximate exemplary luminance of 0 cd/m² for about 1 second, all against an exemplary fixed background luminance of 5.5 cd/m².

Appearing beneath the time course of a stimulus pair in FIG. 13b is the time course of the corresponding cycle-averaged pupillary response curve. The cycle-averaged pupillary response curve shows a graph of the average variation of the horizontal diameter of the pupil, in millimeters, in response to the presentation of a stimulus pair as a function of time, in units of sixtieths of a seconds, e.g., 60 units on the abscissa represents 1 sec; 120 units on the abscissa represents 2 sec, etc.

Referring to FIG. 13b, it can be seen that within an exemplary Type II stimulus cycle, the luminance may be fixed for one exemplary shaped stimulus and varied for the other exemplary shaped stimulus. For example, the stimulus luminance may be about 36 cd/m² for the exemplary shaped inferior light stimulus whenever it is on, and cycled over a plurality of different luminance levels for the exemplary shaped superior stimulus whenever it is on, such as, for example, approximately 24 cd/m², 36 cd/m², and 54 cd/m², each lasting for about 1 second. As shown in FIG. 13b, the presentation of 3 exemplary Type II stimulus pairs, each lasting for about 2 seconds comprise an exemplary Type II stimulus cycle, lasting for 3×2 sec=6 sec.

A Type II stimulus pair presentation is an example of the presentation of a variable-luminance stimulus pair, a plurality of which may comprise a variable-luminance stimulus cycle that may last for a variable-luminance stimulus cycle time. A plurality of variable-luminance stimulus cycles, whose constituent superior and inferior stimuli have the same shape comprise a variable-luminance stimulus set. A selectable number (one or more) of variable-luminance stimulus sets comprise a variable-luminance stimulus test.

If, for example, the number of variable-luminance stimulus cycles is 3, and the variable-luminance stimulus cycle time is about 6 seconds, then a variable-luminance stimulus set will last for a variable-luminance stimulus set time of about 3×6 sec=18 sec. In a variable-luminance stimulus test each variable-luminance stimulus set may present a plurality of variable-luminance stimulus cycles whose superior and inferior stimuli have the same shape within each variable-luminance stimulus set, but may differ from set to set.

For example, a Type II stimulus pair whose superior and inferior stimuli have a first shape may be presented 3 times to form a first variable-luminance stimulus cycle. The first variable-luminance stimulus cycle may be presented 2 more times to form a first variable-luminance stimulus set. The variable-luminance stimulus set may be presented again as a second stimulus set whose constituent stimulus pairs have a second shape. The variable-luminance stimulus set may be presented yet again as a third stimulus set whose constituent stimulus pairs have a third shape. The presentation of the three variable-luminance stimulus sets comprises the presentation the Type II variable-luminance stimulus test.

Alternatively stated, an exemplary Type II variable-luminance stimulus test may be comprised of 3 variable-luminance stimulus sets, each presenting 3 variable-luminance stimulus cycles as follows:

[i] a first variable-luminance stimulus cycle lasting about 6 seconds is presented to an eye, and is repeated 2 more times, for a total of three presentations of, for example, a pre-selected symmetrically paired superior and inferior stimulus having the shape of a paracentral scotoma, thereby forming a first variable-luminance stimulus set lasting 3×6=18 seconds; then,

[ii] a second variable-luminance stimulus cycle lasting about 6 seconds is presented to the same eye, and is repeated 2 more times, for a total of three presentations of, for example, a pre-selected symmetrically paired superior and inferior stimulus having the shape of a Bjerrurn's scotoma, thereby forming a second variable-luminance stimulus set lasting 3×6=18 seconds; then,

[iii] a third variable-luminance stimulus cycle lasting about 6 seconds is presented to the same eye, and is repeated 2 more times, for a total of three presentations of, for example, a pre-selected symmetrically paired superior and inferior stimulus having the shape of a peripheral scotoma, thereby forming a third variable-luminance stimulus set lasting 3×6=18 seconds Thereafter, the same three sets of three repetitions of a variable stimulus cycle may be presented to the other eye for each of the three exemplary pre-selected symmetrically paired superior and inferior stimulus shapes; however, the sequence of presentation of the three exemplary pre-selected symmetrically paired superior and inferior stimulus shapes may differ from that used for the first eye.

Applying the foregoing timing for each of the three sets of variable stimulus cycles presented to an eye in a stimulus test, and allowing a rest time of 30 seconds following the presentation of the first set of three exemplary variable stimulus cycles and following the presentation of the second set of three exemplary variable stimulus cycles, the total time for administering a Type II variable-luminance stimulus test is 18[3×6] sec+30 sec+18[3×6] sec+30 sec+18[3×6] sec=114 sec Stimulus luminance values may be modified in subsequent test sessions based on the results of prior test sessions.

3.22 Computations

In the presentation of either a steady-state-luminance stimulus test or a variable-luminance stimulus test to each eye of a patient, the invention computes:

[i] a pupillary response curve for the stimulus test

[ii] a cycle-averaged pupillary response curve for a representative stimulus cycle of each stimulus set of the stimulus test;

[iii] a cycle-averaged superior pupillary response amplitude Ra (sup) for each stimulus pair of the representative stimulus cycle;

[iv] a corresponding shaped superior stimulus luminance L(sup) for each stimulus pair of the representative stimulus cycle;

[v] a cycle-averaged inferior pupillary response amplitude Ra(inf) for each stimulus pair of the representative stimulus cycle;

[vi] a corresponding shaped inferior stimulus luminance L(inf) for each stimulus pair of the representative stimulus cycle;

[vii] a cycle-averaged pupillary response balance $$RB=[Ra(sup)-Ra(inf)]/[Ra(sup)+Ra(inf)] \quad (4.0)$$

for each stimulus pair of the representative stimulus cycle;
[viii] a luminance ratio $$LR = L(inf)/L(sup) \quad (5.0)$$

or $$LR = L(sup)/L(inf) \quad (6.0)$$

for each stimulus pair of the representative stimulus cycle;

For example, in the presentation to an eye of a variable-luminance stimulus test comprising 1 stimulus set of 3 stimulus cycles, each presenting 3 stimulus pairs, the invention computes
[i] a pupillary response curve for the stimulus test
[ii] a cycle-averaged pupillary response curve for a representative stimulus cycle;
[iii] a cycle-averaged superior pupillary response amplitude $Ra(sup_1)$, $Ra(sup_2)$, $Ra(sup_3)$ for each stimulus pair of the representative stimulus cycle (see FIG. 15a, infra,);
[iv] a corresponding shaped superior stimulus luminance $L(sup_1)$, $L(sup_2)$, $L(sup_3)$ for each stimulus pair of the representative stimulus cycle;
[v] a cycle-averaged inferior pupillary response amplitude $Ra(inf_1)$, $Ra(inf_2)$, $Ra(inf_3)$ for each stimulus pair of the representative stimulus cycle (see FIG. 15a infra,);
[vi] a corresponding shaped inferior stimulus luminance $L(inf_1)$, $L(inf_2)$, $L(inf_3)$ for each stimulus pair of the representative stimulus cycle;
[vii] a cycle-averaged pupillary response balance $$RB_1 = [Ra(sup_1) - Ra(inf_1)]/[Ra(sup_1) + Ra(inf_1)]; \quad (7.0)$$

$$RB_2 = [Ra(sup_2) - Ra(inf_2)]/[Ra(sup_2) + Ra(inf_2)]; \quad (8.0)$$

$$RB_3 = [Ra(sup_3) - Ra(inf_3)]/[Ra(sup_3) + Ra(inf_3)]; \quad (9.0)$$

for each stimulus pair of the representative stimulus cycle;
[viii] a luminance ratio for each stimulus pair of the representative stimulus cycle;

$$LR_1 = L(inf_1)/L(sup_1) \quad (10.0)$$

$$LR_2 = L(inf_2)/L(sup_2) \quad (11.0)$$

$$LR_3 = L(inf_3)/L(sup_3) \quad (12.0)$$

or $$LR_1 = L(sup_1)/L(inf_1) \quad (13.0)$$

$$LR_2 = L(sup_2)/L(inf_2) \quad (14.0)$$

$$LR_3 = L(sup_3)/L(inf_3) \quad (15.0)$$

The luminance of either the exemplary shaped inferior or the exemplary shaped superior stimulus when off may, for example, be substantially dimmed by the invention to a luminance of from about 0.010 cd/m² to about 0.001 cd/m² against a background luminance of about 5 cd/m², and is effectively denominated as 0 cd/m² in both FIG. 13a and FIG. 13b. Alternatively, the luminance of the exemplary shaped inferior light stimulus may be made to vary and the luminance of the exemplary shaped superior light stimulus may be fixed, and vice versa.

3.23 Exemplary Type II Variable-Luminance Stimulus Test Protocol

In administering the exemplary Type II variable-luminance stimulus test, an exemplary stimulus test protocol may implemented as follows:

a. aligning an eye 200 of a patient with stimulus display device 102, pupillometer light source 114 and pupillometer video camera 111, so that the pupil of eye 200 is visualized on pupillometer display device 115 and the patient's test eye is disposed at a distance, such as, for example, about 75 cm, from stimulus pair display device 102 (FIG. 9);
b. occluding the patient's contralateral eye;
c. presenting fixation icon 118 to the patient's eye 200 using stimulus display device 102;
d. instructing the patient to direct the gaze of eye 200 to fixation icon 118;
e. presenting a pre-test stimulus comprising, for example, at least one Type II variable-luminance stimulus cycle, until the patient's PLR reaches a steady oscillatory behavior, as shown on pupillometer video camera 111 and pupillometer display device 115;
f. presenting the Type II variable-luminance stimulus test to the patient on stimulus-pair display device 102 and using the present invention to analyze the patients papillary responses as described supra.;
g. Repeating steps a. to f. for the contralateral eye.

3.24 Pupillary Response Amplitudes

Figure 14A:
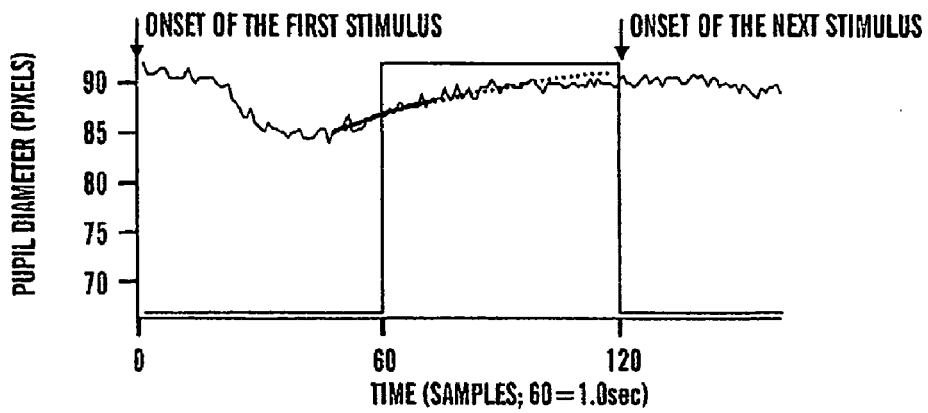
FIG. 14a shows a graph of an exemplary pupillary response to a presentation of two shaped stimuli of fixed luminance.

FIG. 14a shows a graph of an exemplary pupillary response to a presentation of two shaped stimuli of fixed luminance.

Figure 14B:
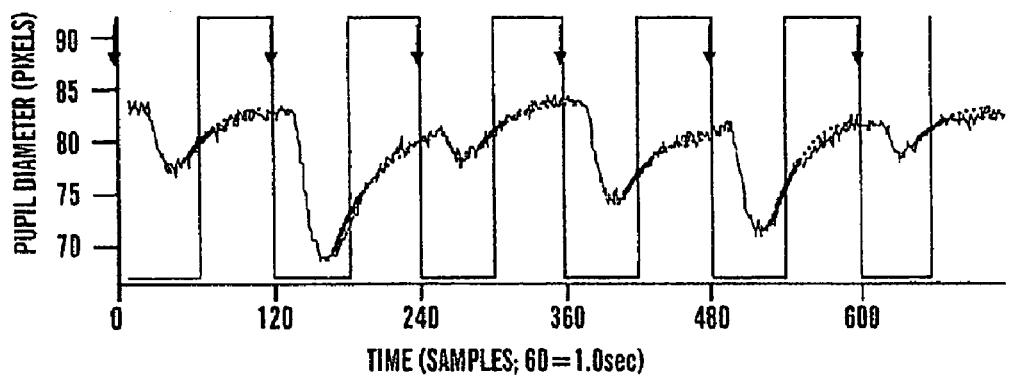
FIG. 14b shows a graph of an exemplary pupillary response to a presentation of repeated shaped stimuli of fixed luminance.

FIG. 14b shows a graph of an exemplary pupillary response to a presentation of repeated shaped stimuli of fixed luminance.

Figure 14C:
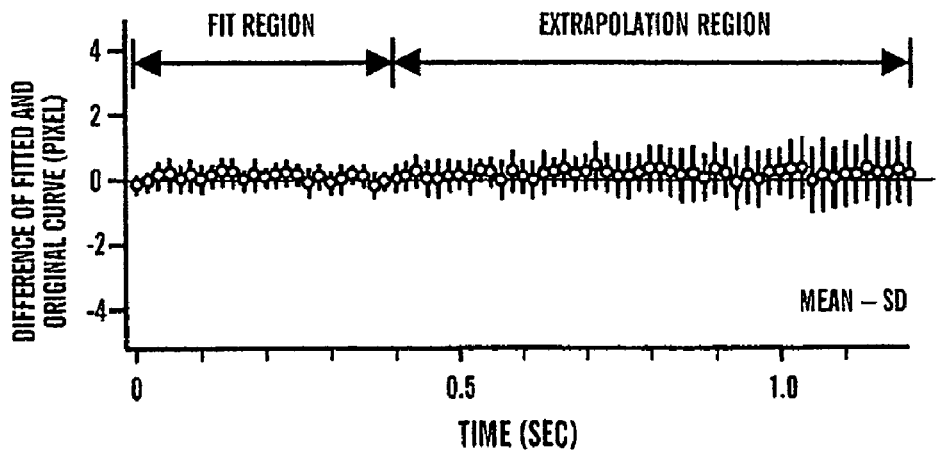
FIG. 14c shows a graph of the mean value (plus or minus a standard deviation) of a difference between a computed pupillary response and a measured pupillary response to a light stimulus of fixed luminance as a function of time as a function of time.

FIG. 14c shows a graph of the mean value (plus or minus a standard deviation) of a difference between a computed pupillary response and a measured pupillary response to a light stimulus of fixed luminance as a function of time as a function of time.

An exemplary set of cycle-averaged superior and inferior pupillary response amplitudes stimulated by the presentation of a Type II stimulus pair is shown in FIG. 15a and FIG. 15b.

In FIG. 14a, the ordinate represents a measure of the diameter of a pupil in pixels, and the abscissa represents time, measured in sixtieths of a second. In FIG. 14a, the graph shows that the variation of the diameter of the pupil in response to the presentation of an exemplary first shaped stimulus lasting about 2 seconds followed by the presentation of an exemplary second shaped stimulus. Downward-pointing vertical arrows indicate the onset of presentation of a shaped stimulus, As shown in FIG. 14a, the pupil begins to constrict within about 12 to 24 sixtieths of a second (about 200-400 ms) after a first shaped stimulus is presented at a constant luminance, and reaches a peak constriction within about 36 to 48 sixtieths of a second (about 600-800 ms) after onset of the first shaped stimulus presentation. Thereafter, the pupil gradually redilates to reach a baseline diameter ("baseline") at about 72 sixtieths of a second (about 1200 ms) after the first shaped stimulus is presented. In the elapsed time from onset of presentation of the first shaped stimulus to about 72 sixtieths of a second (about 1200 ms), the superior or inferior pupillary response amplitude is the difference between the diameter of the pupil before the presentation of the first shaped stimulus and the diameter of the pupil at peak constriction following the presentation of the first shaped stimulus.

However, if, as shown in shown in FIG. 14a, FIG. 14b, and FIG. 15a, a second shaped stimulus is presented before the pupil reaches its baseline, a direct measurement of the pupil's diameter before the onset of the presentation of the second shaped stimulus is difficult, because a response to the first shaped stimulus is still in progress when the second shaped stimulus is presented.

To compute a baseline the pupil of from an immediately previous presentation of a shaped stimulus, a segment of the pupillary graph, shown in FIG. 14a as the thickened solid portion of the graph—from the peak of pupillary constriction (about 600-800 ms after onset of a shaped stimulus presentation) to a point about 400 ms later (about 1000-1200 ms after onset of a shaped stimulus)—is fitted by the invention to an exponential function of time, and the fitted exponential function is extrapolated, to the time of the next peak in pupillary constriction measured by the invention. The pupillary response amplitude is then computed as the difference between the diameter of the pupil measured at peak constriction following the presentation of a shaped stimulus and the baseline the pupil computed from the extrapolation of the exponential function to the time of the peak constriction.

In FIG. 14a, the extrapolation of the fitted exponential function is shown by the dotted extension of the solid portion of the graph. The invention measures the difference between a peak in pupillary constriction following the presentation of a shaped stimulus, and the diameter of the pupil as determined from the extrapolation of the fitted exponential function from the immediately preceding peak in pupillary constriction. The extrapolation is executed repeatedly, throughout a stimulus cycle, as shown in FIG. 14b.

In order to test the accuracy of this fitting process, the inventor modified the stimulus pair used in a Type II stimulus cycle so that each shaped stimulus of a stimulus pair was presented for two seconds instead of one second. In this case, the pupil had enough time to reach a steady-state diameter before its next constriction. A 400 ms sample from the interval from about 800 to about 1200 ms after the onset of presentation of a superior or inferior shaped stimulus was used to perform an extrapolation. The pupillary response to the modified Type II stimulus was then compared to the extrapolation of the fitted exponential function at times near about 1600 ms after the stimulus onset. With the Type II stimulus timing, this is the approximate time of the peak in pupillary constriction in response to the onset of the next stimulus presentation. As shown in FIG. 14c, the difference between the pupillary response to the modified Type II stimulus and the pupillary response determined from the extrapolation of the fitted exponential function was small.

3.25 Computation of Pupillary Response Amplitudes

Generalizing from the discussion of FIG. 14a, and FIG. 14b, each presentation by the invention of either a shaped superior stimulus or a shaped inferior stimulus stimulates a pupillary response, characterized by a constriction of the pupil to a peak constriction followed by a recovery to a steady state constriction. In the course of presenting a plurality of stimulus pairs comprising any stimulus cycle, the invention computes a pupillary response curve comprising a graph of the pupillary responses as a function of time during the course of presentation of the stimulus cycle.

In the presentation by the invention of a stimulus test, the presentations of shaped superior stimuli stimulate pupillary constrictions, for which the invention computes a cycle-averaged superior pupillary response amplitude Ra(sup). In the presentation by the invention of a stimulus test, the shaped inferior stimuli also stimulate pupillary constrictions, for which the invention also computes a cycle-averaged inferior pupillary response amplitude Ra(inf).

Following the presentation by the invention of stimulus pairs comprising a representative stimulus cycle, the cycle-averaged superior pupillary response amplitude is computed as the difference between the cycle-averaged diameter of the pupil measured at peak constriction following the presentation of the shaped superior stimulus and a cycle-averaged baseline computed from an immediately previous presentation of a shaped inferior stimulus.

The computation of the cycle-averaged baseline of the pupil is made by:

[i] fitting an exponential function to a segment of the cycle-averaged pupillary response curve ("fitted time segment") that begins from an antecedent peak constriction time at about the time of peak pupillary constriction during the immediately previous presentation of the shaped inferior stimulus and ends at an antecedent peak extension time, for example, a time about 400 ms after the antecedent peak constriction time; and then,

[ii] extrapolating the fitted exponential function over an extrapolated time segment that begins from the antecedent peak extension time, and ends at an antecedent peak extrapolation time, for example, a time about 800 ms after the antecedent peak constriction time; and,

[iii] selecting as the magnitude of the steady-state baseline diameter of the pupil the extrapolated value of a pupillary diameter at the time of the peak constriction following the presentation of the shaped superior stimulus.

Analogously, in the presentation by the invention of stimulus pairs comprising a representative stimulus cycle, the inferior pupillary response amplitude is computed as the difference between the cycle-averaged diameter of the pupil measured at peak constriction following the presentation of the shaped inferior stimulus and a baseline computed from an immediately previous presentation of a shaped superior stimulus.

Again, the computation of the baseline of the pupil is made by

[i] fitting an exponential function to a segment of the cycle-averaged pupillary response curve ("fitted time segment") that begins from an antecedent peak constriction time at about the time of peak pupillary constriction during the immediately previous presentation of the shaped superior stimulus and ends at an antecedent peak extension time, for example, a time about 400 ms after the antecedent peak constriction time; and then, [ii] extrapolating the fitted exponential function over an extrapolated time segment that begins from the antecedent peak extension time and ends at an antecedent peak extrapolation time, for example, a time about 800 ms after the antecedent peak constriction time; and,

[iii] selecting as the magnitude of the steady-state diameter of the pupil the extrapolated value of the pupillary diameter at the time of the peak constriction following the presentation of the shaped inferior stimulus.

An exemplary set of cycle-averaged superior and inferior pupillary response amplitudes stimulated by the presentation of a Type II stimulus pair is shown in FIG. 15a and FIG. 15b.

FIG. 15a shows a schematic representation of an exemplary Type II stimulus pair as a function of time across a representative stimulus cycle ("time course of a stimulus pair") above a graph (FIG. 15b) of the horizontal diameter of the pupil of an eye of a patient to which the Type II stimulus cycle is being presented as a function of time ("time course of the corresponding pupillary response").

The time course of the exemplary Type II stimulus cycle is schematically shown by two horizontal parallel bars. The upper bar represents the on/off status of an exemplary shaped superior stimulus of the Type II stimulus pair presented to a patient's eye; and, the lower bar represents the on/off status of an exemplary shaped inferior stimulus of the Type II stimulus pair presented to a patient's eye. The bars are accordingly labeled "superior stimulus" and inferior stimulus." Each bar is divided into segments, having an exemplary luminance of the stimulus, measured in cd/m², which is indicated numerically above each segment. The length of each segment in each horizontal bar is proportional to the duration of the stimulus in sixtieths of a second, and corresponds to an abscissa, appearing below, that is scaled in sixtieths of a second.

In FIG. 15a, the superior stimulus bar indicates a shaped superior stimulus presentation to the eye of a patient that is: on at a luminance of $Lsup_1$ (cd/m²) for 1 second, then off at an exemplary luminance of 0 cd/m² for 1 second; then, on again at a luminance of $Lsup_2$ (cd/m²) for 1 second, then off again at an exemplary luminance of 0 cd/m² for 1 second; and, finally on yet again at a exemplary luminance of $Lsup_3$ (cd/m²) for 1 second, then off yet again at an exemplary luminance of 0 cd/m² for 1 second.

In FIG. 15a, the inferior stimulus bar indicates that when the shaped superior stimulus courses through its on/off sequence as described, the shaped inferior stimulus courses through a simultaneous and corresponding sequence of off/on cycles between an exemplary luminance of 0 cd/m² for 1 second and luminance values off $Linf_1$, $Linf_2$, $Linf_3$ cd/m² for 1 second.

Appearing beneath the time course of the exemplary Type II stimulus cycle, in FIG. 15b, is the time course of a corresponding cycle-averaged pupillary response ("cycle-averaged pupillary response curve"). The cycle-averaged pupillary response curve shows a graph of the variation of the horizontal diameter of the pupil, in millimeters, in response to the presentation of the stimulus pairs comprising the exemplary Type II stimulus cycle as a function of time, in units of sixtieths of a second, e.g., 60 units on the abscissa represents 1 sec. Thickened solid portions of the graph represent sequential fits of a an exponential function of time to the graph over sequential fitted time segments indicated on the graph and spanning about 400 ms.

Dotted lines extending from the graph represent sequential extrapolations of each fitted exponential function of time over an extrapolated time segment indicated on the graph.

Vertical line segments labeled $Ra(sup_1)$, $Ra(sup_2)$, $Ra(sup_3)$ represent superior pupillary response amplitudes; and vertical line segments labeled $Ra(inf_1)$, $Ra(inf_2)$, $Ra(inf_3)$ represent inferior pupillary response amplitudes.

3.26 Computing Pupillary Response Balances

As used herein, a cycle-averaged pupillary response balance ("response balance") RR for the presentation of a stimulus pair is defined as:

$$RB=[Ra(sup)-Ra(inf)]/[Ra(sup)+Ra(inf)];\qquad(16.0)$$

where $-1 \leq RB \leq +1$.

For example, the invention may compute a cycle-averaged response balance RB from its measurements of a plurality of pupillary constrictions, such as, for example, the six pupillary constrictions that arise during the presentation of three Type II stimulus pairs comprising a representative Type II stimulus cycle. The six pupillary constrictions comprise one pupillary constriction in response to the onset of each of the exemplary three luminance values of the shaped superior stimulus (e.g., 24, 34, and 48 cd/m²) of the representative Type II stimulus cycle and one pupillary constriction in response to the onset of each of the corresponding fixed luminance values (40 cd/m²) of the shaped inferior lower stimulus of the representative Type II stimulus cycle.

In the exemplary case of three Type II stimulus pairs comprising a representative Type II stimulus cycle the response balance for each stimulus pair is:

$$RB_i=[Ra(sup_i)-Ra(inf_i)]/[Ra(sup_i)+Ra(inf_i)]\qquad(17.0)$$

$inf_i$ (i=1, 2, 3): $i^{th}$ stimulus shaped inferior stimulus
$R(inf_i)$ (i=1, 2, 3): pupillary constriction resulting from $inf_1$
$sup_i$ (i=1, 2, 3): $i^{th}$ stimulus shaped superior stimulus
$R(sup_i)$ (i=1, 2, 3) pupillary constriction resulting from $sup_i$ 3.27 Computing a Balanced Pupillary Response A retina with normal visual function generates a "balanced pupillary response," associated with a response balance RB of about zero. That is, in a normal retina, the presentation of a shaped superior stimulus of a stimulus pair to the superior retina stimulates a superior pupillary response amplitude Ra(sup) about equal to the inferior pupillary response amplitude Ra(inf) that is stimulated by the presentation of a shaped inferior stimulus of a stimulus pair to the inferior retina, making the response balance RB about equal to zero, a value consistent with a balanced pupillary response.

If the superior retina has an abnormal visual sensitivity relative to the inferior retina, then the superior pupillary response amplitude Ra(sup) is likely to be less than the inferior pupillary response amplitude Ra(inf) making the response balance RB less than zero, a value consistent with a superior visual field defect.

If the inferior retina has an abnormal visual sensitivity relative to the superior retina, then the superior pupillary response amplitude Ra(sup) is likely to be greater than the inferior pupillary response amplitude Ra(inf) making the response balance RB greater than zero, a value consistent with an inferior visual field defect.

Since glaucoma has a tendency to affect the retina asymmetrically above and below the horizontal meridian, glaucomatous retinal nerve damage is unlikely to be associated with a balanced pupillary response, and is likely to be associated with a non-zero pupillary response balance, whose sign is indicative of the retinal hemifield in which a visual field defect is likely to be found.

3.28 Evaluation of Diffuse Visual Field Losses

While a balanced pupillary response militates against asymmetric retinal nerve damage that is typical of glaucoma, it is still possible for a patient to have glaucomatous retinal nerve damage that is substantially symmetric with respect to the horizontal meridian. This situation may arise when the retinal nerve damage from glaucoma manifests as a diffuse visual field loss or a generalized depression of the entire visual field.

The cycle-averaged pupillary response amplitudes measured by the present invention $Ra(sup_i)$, $Ra(inf_i)$ may be used to determine the presence of a diffuse visual field loss or generalized depression of the entire visual field in a patient.

For example, as described supra., a Type I stimulus pair whose superior and inferior stimuli have a fixed shape may be presented 3 times to form a steady state stimulus cycle. The steady state stimulus cycle may be presented 2 more times to form a Type I steady state stimulus set. In this example, the single presentation of a Type I steady state stimulus set comprises the presentation of a Type I steady state stimulus test. The cycle-averaged superior pupillary response amplitudes $Ra(sup_1)$, $Ra(sup_2)$, $Rd(sup_3)$ computed by the invention may again be averaged to obtain a "test" superior pupillary response amplitude testRa(sup); and the cycle-averaged inferior pupillary response amplitudes $Ra(inf_1)$, $Ra(inf_2)$, $Ra(inf_3)$ computed by the invention may again be averaged to obtain a "test" inferior pupillary response amplitude testRa (inf).

The test superior pupillary response amplitude testRa(sup) and the test inferior pupillary response amplitude testRa(inf) may each be compared to mean normal values for these parameters as described in section 3.8, supra. If the test superior pupillary response amplitude testRa(sup) computed by the invention is, for example, more than two standard deviations from its corresponding mean normal value, a diffuse superior visual field loss is indicated. If the test inferior pupillary response amplitude testRa(inf) computed by the invention is, for example, more than two standard deviations from its corresponding mean normal value, a diffuse inferior visual field loss is indicated.

3.29 Screening for Visual Field Defects Using a Pupillary Response Balance

The exemplary Type I stimulus pair may be utilized in an exemplary screening test administered by the invention. In the exemplary screening test, all luminances of the exemplary Type I stimulus pair in the "on" state are fixed at the same value, such as, for example 36 cd/m$^2$; and, the Type I stimulus pair is presented against an exemplary background luminance of, for example, 5 cd/m$^2$. In the exemplary screening test, all luminances of the exemplary Type I stimulus pair in the "off" state are fixed at very low luminance, as described supra.

The exemplary screening stimulus test may comprise the presentation of one exemplary screening stimulus set of three exemplary screening stimulus cycles.

The first exemplary screening stimulus cycle may comprise a 1-second presentation of an inferior shaped stimulus of a stimulus pair having the shape of a paracentral scotoma, followed by the three 2-second presentations of stimulus pairs whose constituent shaped superior and inferior stimuli all have the form of a paracentral scotoma.

The second exemplary screening stimulus cycle may comprise a 1-second presentation of an inferior shaped stimulus of a stimulus pair having the shape of a Bjerrum's scotoma, followed by three 2-second presentation of stimulus pairs whose constituent shaped superior and inferior stimuli all have the shape of a Bjerrum's scotoma.

The third exemplary screening stimulus cycle may comprise a 1-second presentation of an inferior shaped stimulus of a stimulus pair having the shape of a peripheral scotoma, followed by the three 2-second presentations of stimulus pairs whose constituent shaped superior and inferior stimuli all have the shape of a peripheral scotoma.

The exemplary screening stimulus test may be represented symbolically as follows:

1$^{st}$ screening stimulus cycle lasting 7 seconds using a paracentral scotoma shape: [inferior, superior, inferior, superior, inferior, superior, inferior]$_{paracentral}$ 2nd screening stimulus cycle lasting 7 seconds using a Bjerrum's scotoma shape: [inferior, superior, inferior, superior, inferior, superior, inferior]$_{Bjerrum}$ 3rd screening stimulus cycle lasting 7 seconds using a peripheral scotoma shape: [inferior, superior, inferior, superior, inferior, superior, inferior]$_{peripheral}$ The three screening stimulus cycles are presented as a single screening stimulus set (test) lasting 3×7 second=21 seconds.

The pupillary response curve recorded over the presentation time of the stimulus set maybe separated into 3 pupillary response data segments of 7 seconds each, corresponding to screening stimulus cycle time of the first, second and third exemplary stimulus cycles.

The first second of the pupillary response data in each exemplary 7-second screening stimulus cycle—corresponding to the first inferior shaped stimulus—is discarded, leaving three 6-second segment of pupillary response data.

Each 6-second pupillary response data segment may be further divided into three 2-second segments of pupillary response data; and, the data from these three segments data are averaged to yield a single 2-second averaged segment of pupillary response data, from which there is computed one superior pupillary response amplitude, one inferior pupillary response amplitude and one response balance. The averaging process will accordingly produce 3 triplets of pupillary response data, each comprising a superior screening pupillary response amplitude, an inferior screening pupillary response amplitude and a screening response balance, which triplets respectively correspond to a paracentral scotoma, a Bjerrum's scotoma and a peripheral scotoma.

The values of the superior screening pupillary response amplitude, the inferior screening pupillary response amplitude and the screening response balance in each data triplet may then be respectively compared to normative data for superior pupillary response amplitudes, inferior pupillary response amplitudes and response balances gathered from populations of normal patients, and an interpretation of the triplet data for screening purposes may be made by reference to the standard deviations from the respective means of such normative data.

3.30 Computing a Luminance Ratio

As used herein, a "luminance ratio"

LR is defined as the ratio of the luminance of a shaped inferior stimulus L(inf) to the luminance of a superior shaped stimulus L(sup):

$$LR = L(inf)/L(sup) \tag{18.0}$$

Contrast values, representing the difference between the luminance of a shaped stimulus and the fixed luminance of a background against which a shaped luminance is presented may be substituted in computations involving the luminance values L(inf)/L(sup)

3.31 Correlation of Response balances and Luminance Ratios

In the present invention, a patient's cycle-averaged response balances RB are effectively plotted against the luminance ratios LR with which they are associated, for example, by maintaining the luminance of a shaped superior stimulus at a fixed value and varying the luminance of the shaped inferior stimulus. The present invention fits cycle-averaged response balances RB to a sigmoid function of luminance ratios LR, of the form $$RB = [L(inf)/L(sup_0)]^a - 1]/[L(inf)/L(sup_0)]^a + 1] \tag{19.0}$$

where L(inf) is the variable luminance of the shaped inferior stimulus; and L(sup$_0$) is the fixed luminance of the shaped superior stimulus, thereby forming a stimulus pair response curve.

In the present invention a patient's cycle-averaged response balances RB may also be effectively plotted against the luminance ratios LR with which they are associated, for example, by maintaining the luminance of a shaped inferior stimulus at a fixed value and varying the luminance of the shaped superior stimulus. The plot of the response balances RB may also be fitted to a sigmoid function of luminance ratios LR, of the form $$RB = [L(sup)/L(inf_0)]^a - 1]/[L(sup)/L(inf_0)]^a + 1] \tag{20.0}$$

where L(sup) is the variable luminance of the shaped superior stimulus; and L(inf₀) is the fixed luminance of the shaped inferior stimulus, thereby also forming a stimulus pair response curve.

FIG. 15c is an exemplary graph of a patient's cycle-averaged response balances RB fitted to a sigmoid function of luminance ratios LR, ("stimulus pair response curve") where the abscissa is scaled in units of the logarithm of the luminance ratios.

3.32 Computing a Balanced Luminance Response

If the visual sensitivity of the superior retina and the visual sensitivity of the inferior retina of an eye are about equal ("symmetric visual sensitivity"), then, on average, the luminance ratio LR required to elicit a balanced pupillary response (a "balanced luminance ratio" LRbal, at which RB=Rbal=0) will be 1; and, the logarithm of the balanced luminance ratio will be zero; i.e., $$\log [\text{LRbal}=1]=0 \tag{21.0}$$

If the visual sensitivity of the superior retina and the visual sensitivity of the inferior retina of an eye are not about equal ("asymmetric visual sensitivity"), then, on average, the balanced luminance ratio LRbal will be other than 1, and the logarithm of the balanced luminance ratio LRbal will be non-zero; i.e., $$\log [\text{LRbal} \neq 1] \neq 0 \tag{22.0}$$

Accordingly, as shown in FIGS. 16a through 16c, the value of the magnitude of the balance luminance ratio LRbal associated with any pupillary response to a stimulus pair presentation computed by the present invention comprises an index of the deviation of the computed pupillary response from a normal pupillary response to the stimulus pair presentation.

If the value of the balanced luminance ratio is LRbal outside of a selectable range of normal then a visual field defect is indicated. If the value of the balanced luminance ratio equals or exceeds the upper normal limit, a visual field defect is indicated in the superior retina. If the value of the balanced luminance ratio is less than or equals the upper normal limit, then a visual field defect is indicated in the inferior retina.

The selectable range of normal is determined statistically. For example, if the distribution of the average values of the logarithm of the balanced luminance ratios for normal eyes is a normal distribution centered at 0, with a standard deviation (SD) of 0.080 log units (0.80 dB) then, a patient whose left eye is determined by the invention to have a balanced luminance ratio with an average value of, for example, either equal to or greater than +0.24 log units (+2.4 dB), or equal to or less than −0.24 log units (−2.4 dB), will have a balanced luminance ratio that is ≧3 SD away from the center of the distribution, corresponding to a 99.75% likelihood that the tested area of his or her retina is abnormal.

FIGS. 16a through 16c show three exemplary graphs of the pupillary response balances of three different patients fitted to sigmoid functions of luminance ratios and plotted against abscissas scaled in logarithmic units of the luminance ratios (stimulus pair response curves), from which balanced luminance ratios associated with balanced pupillary response balances have been derived. In each graph $x_0$ is the x-coordinate of the intersection of the fitted sigmoid curve with the horizontal line representing the state of pupillary balance at which RB=1. Accordingly, in each graph, the value of $x_0$ is the balanced luminance ratio for the patient.

FIG. 16a shows an exemplary graph of the pupillary response balances RB of a normal patient fitted to a sigmoid function of the luminance ratios LR in log units (stimulus pair response curve) associated with that patient's pupillary response balances.

The graph is labeled "Normal Ra(sup)≈Ra(inf) Rbal≈0." FIG. 16a shows that $x_0$, the balanced luminance ratio is about zero (−0/25 to +0.25 log units), a value found to be consistent with a distribution of balanced luminance ratios obtained by the inventor for normal patients.

FIG. 16b shows an exemplary graph of the pupillary response balances RB of a patient with a superior visual field defect fitted to a sigmoid function of the luminance ratios LR in log units (stimulus pair response curve) associated with that patient's pupillary response balances. The graph is labeled "Upper Visual Field Defect Ra(sup)<Ra(inf) Rbal≈−1." FIG. 16b shows that $x_0$, the balanced luminance ratio is far greater than zero, a value found to be consistent with a distribution of balanced luminance ratios obtained by the inventor for patients' having a superior visual field defect with a concomitant diminution in the amplitude of the pupillary response to the presentation of a shaped superior light stimulus relative to the amplitude of the pupillary response to the presentation of the shaped inferior stimulus—a condition that might result from damage to the inferior retina.

FIG. 16c shows an exemplary graph of the pupillary response balances RB of a patient with an inferior visual field defect fitted to a sigmoid function of the luminance ratios LR in log units (stimulus pair response curve) associated with that patient's pupillary response balances. The graph is labeled "Lower Visual Field Defect Ra(sup)>Ra(inf) Rbal≈+1." FIG. 16c shows that $x_0$, the balanced luminance ratio is far less than zero, a value found to be consistent with a distribution of balanced luminance ratios obtained by the inventor for patients' having an inferior visual field defect with a concomitant diminution in the amplitude of the pupillary response to the presentation of a shaped inferior light stimulus relative to the amplitude of the pupillary response to the presentation of the shaped superior stimulus—a condition that might result from damage to the superior retina.

While the foregoing invention has been described in some detail for purposes of clarity and understanding, it will be appreciated by one skilled in the art, from a reading of this disclosure, that variations or modifications in form and detail can be made without departing from the scope of the invention. Such variations or modifications are not to be regarded as a departure from the scope of the invention and all such variations modifications are intended to be included within the scope of the following claims.

I claim:

1. An apparatus for measuring visual sensitivity of a retina of an eye, said apparatus comprising:
   a stimulus presentation device;
   a pupillometer; and
   a computer system programmed to:
   (1) present through the stimulus presentation device a stimulus test to said eye, said stimulus test including a stimulus pair made up of a first stimulus and a second stimulus for illuminating areas within first and second regions of the retina, wherein the first stimulus illuminates an area within the first region but not any area within the second region and the second stimulus illuminates an area within the second region but not any area within the first region, and wherein the first and second regions of the retina are spatially separated from each other;
   (2) use the pupillometer to measure a pupillary response of the eye based on the stimulus test; and (3) from the measured papillary response, generate a pupillary response curve for said stimulus test.

2. The apparatus of claim 1, wherein the stimulus presentation device comprises a display device.

3. The apparatus of claim 1, wherein pupillometer comprises a light source for illuminating the pupil of the eye and a camera for monitoring the eye.

4. The apparatus of claim 1, wherein said stimulus test comprises a stimulus set.

5. The apparatus of claim 4, wherein said stimulus set comprises a stimulus cycle.

6. The apparatus of claim 1, wherein the first stimulus is a shaped superior stimulus and the second stimulus is of a shaped inferior stimulus that is a horizontal mirror image of the shaped superior stimulus.

7. The apparatus of claim 6, wherein the computer system is further programmed to compute from said pupillary response curve a cycle-averaged pupillary response curve for a representative stimulus cycle.

8. The apparatus of claim 7, wherein the computer system is further programmed to use said cycle-averaged pupillary response curve to compute a cycle-averaged superior pupillary response amplitude and a corresponding shaped superior stimulus luminance for the representative stimulus pair of said representative stimulus cycle.

9. The apparatus of claim 8, wherein the computer system is further programmed to use said cycle-averaged pupillary response curve to compute a cycle-averaged inferior pupillary response amplitude and a corresponding shaped inferior stimulus luminance for the representative stimulus pair of said representative stimulus cycle.

10. The apparatus of claim 9, wherein said shaped superior stimulus and said shaped inferior stimulus are characterized by selectable shapes, areas, luminances and presentation times.

11. The apparatus of claim 10, wherein said selectable shapes encompass the shape of a visual field defect.

12. The apparatus of claim 11, wherein said visual field defect conforms to a visual field defect that is characteristic of glaucoma.

13. The apparatus of claim 11, wherein said visual field defect is selected from the group comprising a central scotoma, a paracentral scotoma, an altitudinal scotoma, a Bjerrum's scotoma, a peripheral scotoma, a nasal step, an arcuate scotoma and a generalized visual field defect.

14. The apparatus of claim 11, wherein the computer system is further programmed to display said stimulus pair upon said display device for presentation to said eye and having a selectable background luminance.

15. The apparatus of claim 11, wherein said stimulus pair encompasses at least a central 20° of a visual field of said eye.

16. The apparatus of claim 11, wherein said stimulus test comprises a Type II variable-luminance test.

17. The apparatus of claim 11, wherein said stimulus test comprises a Type I steady-state-luminance test.

* * * * *